US009546440B2

(12) United States Patent
Mitsuno et al.

(10) Patent No.: US 9,546,440 B2
(45) Date of Patent: *Jan. 17, 2017

(54) NONWOVEN FABRIC, AND METHOD FOR PRODUCING NONWOVEN FABRIC

(75) Inventors: Satoshi Mitsuno, Kagawa (JP); Jun Okuda, Kagawa (JP)

(73) Assignee: Unicharm Corporation, Ehime (JP)

( * ) Notice: Subject to any disclaimer, the term of this patent is extended or adjusted under 35 U.S.C. 154(b) by 199 days.

This patent is subject to a terminal disclaimer.

(21) Appl. No.: 14/003,073

(22) PCT Filed: Feb. 24, 2012

(86) PCT No.: PCT/JP2012/055307
§ 371 (c)(1),
(2), (4) Date: Sep. 4, 2013

(87) PCT Pub. No.: WO2012/121123
PCT Pub. Date: Sep. 13, 2012

(65) Prior Publication Data
US 2013/0344286 A1 Dec. 26, 2013

(30) Foreign Application Priority Data
Mar. 4, 2011 (JP) ................................ 2011-048298

(51) Int. Cl.
*D04H 1/4382* (2012.01)
*D04H 1/495* (2012.01)
(Continued)

(52) U.S. Cl.
CPC .......... *D04H 1/4382* (2013.01); *A61F 13/513* (2013.01); *A61F 13/51108* (2013.01);
(Continued)

(58) Field of Classification Search
CPC .................................................... D04H 1/4382
See application file for complete search history.

(56) References Cited

U.S. PATENT DOCUMENTS 6,673,418 B1   1/2004   DeOlivera et al.
8,974,890 B2 * 3/2015   Mitsuno ...................... 428/152
                        (Continued)

FOREIGN PATENT DOCUMENTS

EP    1 022 033 A1   7/2000
JP    2002-187228 A  7/2002
                    (Continued)

OTHER PUBLICATIONS

International Search Report from corresponding PCT application No. PCT/JP2012/055307 dated May 29, 2012 (2 pgs).

*Primary Examiner* — William P Watkins, III
(74) *Attorney, Agent, or Firm* — Brinks Gilson & Lione

(57) ABSTRACT

A nonwoven fabric comprising extendable fiber and elastic fiber, wherein the nonwoven fabric comprises a first side having a plurality of protrusions and a plurality of recesses and a second side on the side opposite the first side, the proportion of extendable fiber in the protrusions on the first side is higher than the proportion of extendable fiber in the recesses on the first side, and the nonwoven fabric is coated with a hydrophilic agent, or the extendable fiber and elastic fiber comprise a hydrophilic agent, the nonwoven fabric has a water absorbing property represented by a water absorption height of at least 10 mm in a water absorption test, and a quick-drying property represented by a transpiration rate of at least 20 mass % in a transpiration test.

19 Claims, 7 Drawing Sheets

(51) Int. Cl.
*D04H 1/736* (2012.01)
*D06C 3/00* (2006.01)
*D06C 15/00* (2006.01)
*D06C 23/04* (2006.01)
*D06C 29/00* (2006.01)
*A61F 13/513* (2006.01)
*D04H 1/54* (2012.01)
*A61F 13/511* (2006.01)
*D04H 1/4291* (2012.01)
*D04H 1/435* (2012.01)
*D04H 1/4358* (2012.01)

(52) U.S. Cl.
CPC ........... *D04H 1/4291* (2013.01); *D04H 1/435* (2013.01); *D04H 1/4358* (2013.01); *D04H 1/495* (2013.01); *D04H 1/54* (2013.01); *D04H 1/736* (2013.01); *D06C 3/00* (2013.01); *D06C 15/00* (2013.01); *D06C 23/04* (2013.01); *D06C 29/00* (2013.01); *Y10T 428/24273* (2015.01); *Y10T 428/24322* (2015.01); *Y10T 428/24521* (2015.01); *Y10T 428/24603* (2015.01)

(56) References Cited

U.S. PATENT DOCUMENTS

| | | | |
|---|---|---|---|
| 2002/0028324 A1* | 3/2002 | Yamaki et al. | 428/294.7 |
| 2002/0068150 A1 | 6/2002 | Taneichi et al. | |
| 2004/0214498 A1* | 10/2004 | Webb et al. | 442/329 |
| 2008/0044622 A1 | 2/2008 | Noda et al. | |
| 2010/0209667 A1 | 8/2010 | Mitsuno et al. | |
| 2011/0046586 A1 | 2/2011 | Kawakami et al. | |
| 2012/0164908 A1 | 6/2012 | Kunimoto | |
| 2013/0034686 A1 | 2/2013 | Mitsuno et al. | |

FOREIGN PATENT DOCUMENTS

| | | |
|---|---|---|
| JP | 2008-25080 A | 2/2008 |
| JP | 2008-246995 A | 10/2008 |
| JP | 2008-248460 A | 10/2008 |
| JP | 2009-62650 A | 3/2009 |
| JP | 2009-155741 A | 7/2009 |
| JP | 2010-168715 A | 8/2010 |
| JP | 2011-226011 A | 11/2011 |
| WO | WO 2007/148499 A1 | 12/2007 |
| WO | WO 2011-016343 | 2/2011 |

* cited by examiner (a)

(b)

NONWOVEN FABRIC, AND METHOD FOR PRODUCING NONWOVEN FABRIC

RELATED APPLICATION

This application is a 35 U.S.C. §371 national phase filing of International Patent Application No. PCT/JP2012/055307, filed Feb. 24, 2012, through which and to which priority is claimed under 35 U.S.C. §119 to Japanese Patent Application No. 2011-048298, filed Mar. 4, 2011.

TECHNICAL FIELD

The present disclosure relates to a nonwoven fabric, and a method for producing the same.

BACKGROUND ART

Nonwoven fabrics are used in absorbent articles, such as sanitary products and disposable diapers, cleaning products, such as wipers, and medical goods, such as masks, and such products employ nonwoven fabrics with performance suitable for the purpose of the products and their intended location of use.

With absorbent articles, for example, it is necessary to employ nonwoven fabrics that expand and contract in response to bodily movement during wear or use, without creating an uncomfortable feeling for the user. Disposable diapers require nonwoven fabrics with high elasticity and strength sufficient to prevent tearing during extension, as well as satisfactory feel on the skin and air permeability.

PTL 1 discloses, as a nonwoven fabric with excellent air permeability, a three-dimensional sheet material comprising a material having a first layer and a second layer adjacent thereto, the first layer and second layer being partially bonded by joining sections in a prescribed pattern, the first layer forming a three-dimensional spatial shape between the joining sections, the second layer being composed of a material exhibiting elastomeric behavior, and the entire sheet also exhibiting elastomeric behavior as well as having air permeability. In the spatial sheet material described in PTL 1, the fibers composing the second layer are heat treated above the temperature at which heat shrinkage begins to cause shrinkage of the second layer, thereby creating a spatial structure.

CITATION LIST

Patent Literature

PTL 1 Japanese Unexamined Patent Publication No. 2002-187228

SUMMARY OF INVENTION

Technical Problem

However, since the spatial sheet material described in PTL 1 exhibits a spatial structure by shrinkage of the second layer, it has excellent air permeability in the planar direction of the sheet material but tends to lack air permeability in the thickness direction. Also, because the spatial sheet material described in PTL 1 has shrinkage of the second layer, the fiber density of the second layer is especially high and elasticity is more easily inhibited.

It is therefore an object of the present disclosure to provide a nonwoven fabric with excellent feel on the skin and elasticity, excellent air permeability in the planar direction and the thickness direction, and high water absorbing and quick-drying properties, as well as a method for producing the nonwoven fabric.

Solution to Problem

As a result of diligent research directed toward solving the problems described above, the present inventors have found that the aforementioned problems can be solved by a nonwoven fabric comprising extendable fiber and elastic fiber, wherein the nonwoven fabric comprises a first side having a plurality of protrusions and a plurality of recesses and a second side on the side opposite the first side, the proportion of extendable fiber in the protrusions on the first side is higher than the proportion of extendable fiber in the recesses on the first side, and the nonwoven fabric is coated with a hydrophilic agent or the extendable fiber and elastic fiber comprise a hydrophilic agent, the nonwoven fabric has a water absorbing property represented by a water absorption height of at least 10 mm in a water absorption test, and a quick-drying property represented by a transpiration rate of at least 20 mass % in a transpiration test.

Advantageous Effects of Invention

The nonwoven fabric comprising extendable fiber and elastic fiber in accordance with the disclosure has excellent air permeability in the planar direction and the thickness direction, and has high water absorbing and quick-drying properties.

The nonwoven fabric comprising extendable fiber and elastic fiber of the disclosure also has excellent feel on the skin and elasticity.

DESCRIPTION OF EMBODIMENTS

The nonwoven fabric comprising extendable fiber and elastic fiber of the disclosure, and the method for producing the nonwoven fabric, will now be explained in detail.

[Nonwoven Fabric Comprising Extendable Fiber and Elastic Fiber]

Figure 1:
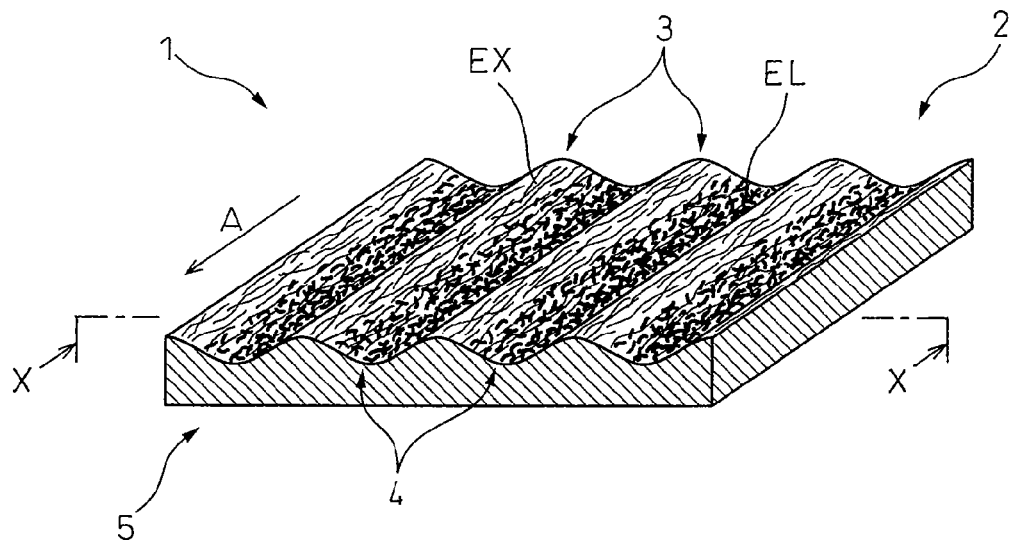
FIG. 1 is a schematic view of a nonwoven fabric comprising extendable fiber and elastic fiber in accordance with an embodiment of the disclosure.

FIG. 1 is a schematic view of the nonwoven fabric comprising extendable fiber and elastic fiber in accordance with an embodiment of the disclosure. The nonwoven fabric comprising extendable fiber and elastic fiber 1, shown in FIG. 1, has a plurality of protrusions 3 and a plurality of recesses 4 on a first side 2. In the nonwoven fabric comprising extendable fiber and elastic fiber 1 shown in FIG. 1, the protrusions 3 are rich in extendable fiber EX while the recesses 4 are rich in elastic fiber EL, and the proportion of extendable fiber in the protrusions 3 is greater than the proportion of extendable fiber in the recesses 4. Also, in the nonwoven fabric comprising extendable fiber and elastic fiber 1 shown in FIG. 1, the protrusions 3 and the recesses 4 are both parallel to the first direction A, and are alternately situated in the direction perpendicular to the first direction A.

In the embodiment shown in FIG. 1, the extendable fiber EX in the protrusions 3 have orientation along the first direction A, while the elastic fiber EL in the recesses 4 have no particular orientation. Also, the extendable fiber EX in the embodiment of FIG. 1, while not shown, is oriented in the thickness direction of the nonwoven fabric 1. In the protrusions 3, the compactness of the fibers tends to be higher than at the other locations. The orientation in the thickness direction and the compactness of the fibers will now be explained in regard to the method for producing a nonwoven fabric comprising extendable fiber and elastic fiber.

The hydrophilic agent is not shown in FIG. 1.

As used herein, the "proportion of extendable fiber" is the mass ratio of extendable fiber at a given location with respect to the total fiber. The proportion may be measured by any desired method so long as the method allows estimation of the mass ratio of the extendable fiber, and the following solvent method is an example.

(1) Fiber is sampled from a protrusion on the first side of the nonwoven fabric comprising extendable fiber and elastic fiber, and weighed.

(2) The sample fiber is dissolved in a solvent capable of dissolving either the extendable fiber or the elastic fiber, and is allowed to stand for a fixed period of time, such as 30 minutes.

(3) The solution is filtered out, the remaining fiber is rinsed if necessary, and the remaining fiber is dried.

(4) The dry mass of the remaining fiber is measured and the mass ratio of the fiber is calculated.

The solvent may be selected as appropriate, and for example, when the extendable fiber is a polyolefin and the elastic fiber is a polyurethane-based elastomer, a solvent, such as dimethylacetamide or dimethylformamide may be selected in which the polyurethane-based elastomer is soluble and the polyolefin is insoluble. When the elastic fiber is a polystyrene-based elastomer, a solvent, such as toluene or xylene may be selected as a solvent in which it is soluble.

The proportion of extendable fiber may be measured for the recesses on the first side, as well as the protrusions and recesses on the second side, as desired.

A separate method for measuring the proportion of extendable fiber is the following dyeing method.

(1) The nonwoven fabric comprising extendable fiber and elastic fiber is dyed with a dye having a different dye affinity for the extendable fiber than the dye affinity for the elastic fiber.

(2) An optical microscope or the like is used to record a projection image of the protrusions on the first side.

(3) The proportion of extendable fiber is evaluated visually based on the image, or the image is binarized to distinguish between the extendable fiber and elastic fiber, and the proportion of extendable fiber is calculated.

This dyeing method is preferred for measuring the proportion of extendable fiber in nonwoven fabrics where a solvent method is not suitable.

The proportion of extendable fiber may be measured for the recesses on the first side, as well as the protrusions and recesses on the second side, as desired.

In the dyeing method described above, the proportion obtained by binarizing is the area ratio in the projection image, and since this area ratio roughly corresponds to the volume ratio, multiplying it by the density of the fiber allows the mass ratio to be calculated.

From the viewpoint of the effect of the disclosure, and especially both the feel on the skin and elasticity, the proportion of extendable fiber in the protrusions on the first side is preferably at least 1 mass % higher, more preferably at least 2 mass % higher, even more preferably at least 3 mass % higher and yet more preferably at least 5 mass % higher than the proportion of extendable fiber in the recesses on the first side.

A nonwoven fabric comprising extendable fiber and elastic fiber, such as shown in FIG. 1 has a proportion of extendable fiber in the protrusions on the first side that is higher than the proportion of extendable fiber in the recesses on the first side, and it therefore exhibits excellent feel on the skin and excellent elasticity. The reason for this is as follows.

In general terms, elastic fiber is a component that imparts elasticity to a nonwoven fabric, but it also has the disadvantage of an inferior feel on the skin including tack and high friction, while extendable fiber has virtually no elasticity but an excellent feel on the skin. The nonwoven fabric comprising extendable fiber and elastic fiber of the disclosure has extendable fiber with an excellent feel on the skin situated in the protrusions that contact the human body, while elastic fiber that has a poor feel on the skin is situated essentially uniformly in the recesses and inside the protrusions of the nonwoven fabric that do not easily contact the body, and therefore it has both elasticity and an excellent feel on the skin.

The nonwoven fabric comprising extendable fiber and elastic fiber, as shown in FIG. 1, has numerous recesses with low thickness and low aeration resistance in the thickness direction on the first side, and it therefore exhibits more excellent air permeability in the thickness direction of the nonwoven fabric than a nonwoven fabric without recesses. The nonwoven fabric comprising extendable fiber and elastic fiber shown in FIG. 1 also has numerous recesses that can serve as passageways for air in the planar direction on the first side, and therefore exhibits excellent air permeability in the planar direction of the nonwoven fabric.

As used herein, "elastic fiber" means fiber that is capable of elastic stretching. More specifically, the elastic fiber is fiber that has a larger elastic limit than the stress applied during formation and during expected use, and that is capable of elastic stretching within the range of stress during formation and during expected use. Examples of elastic fiber materials include polyurethane-based elastomers, polystyrene-based elastomers, polyolefin-based elastomers, polyamide-based elastomers, polyester-based elastomers, and combinations thereof. The elastic fiber is preferably a polyurethane-based elastomer, from the viewpoint of low distortion after stretching and high heat resistance.

The fiber diameter of the elastic fiber is preferably in the range of 2-50 μm and more preferably in the range of 15-30 μm.

In the nonwoven fabric comprising extendable fiber and elastic fiber in accordance with an embodiment of the disclosure, the elastic fiber preferably comprises a hydrophilic agent in order to obtain high water absorbing and quick-drying properties, and has hydrophilicity. An example of elastic fiber comprising a hydrophilic agent is elastic fiber formed by mixing a hydrophilic agent with an elastic fiber material and then spinning it, also referred to as hydrophilic agent-kneaded elastic fiber.

The hydrophilic agent used in the elastic fiber may be the same hydrophilic agent used to coat the nonwoven fabric, described hereunder, or a different agent.

As used herein, "extendable fiber" means fiber having a smaller elastic limit than the elastic limit of the aforementioned elastic fiber. More specifically, the extendable fiber is fiber having a smaller elastic limit than the stress applied during formation of the nonwoven according to the disclosure, and capable of plastic deformation by the stress applied during formation of the nonwoven according to the disclosure. The extendable fiber becomes thinner and longer by plastic deformation. As used herein, extendable fiber that has undergone plastic deformation by the stress of formation will sometimes be referred to as "stretched extendable fiber". An example of stretched extendable fiber is fiber having a uniform diameter, or fiber having a non-uniform diameter, such as one having partial thin sections (necking sections).

Examples of extendable fiber materials include fibers made of polyolefins, such as polyethylene and polypropylene, and polystyrenes, polyesters, polyamides, polyurethanes and polylactic acids, and combinations thereof. The extendable fiber may be composite fiber, such as core-sheath fiber or side-by-side fiber. The extendable fiber may be fiber that is essentially hydrophilic, such as natural and/or semi-natural fiber.

The extendable fiber is preferably fiber comprising polypropylene and polyethylene, from the viewpoint of low crystallinity and high ductility.

The fiber diameter of the extendable fiber is preferably in the range of about 1 to about 40 μm, and more preferably in the range of about 5 to about 25 μm. The fiber diameter of the extendable fiber is also preferably smaller than the fiber diameter of the elastic fiber. This will allow flexibility, high bulk and a masking property to be imparted to the nonwoven fabric comprising extendable fiber and elastic fiber.

In the nonwoven fabric comprising extendable fiber and elastic fiber in accordance with an embodiment of the disclosure, the extendable fiber preferably comprises a hydrophilic agent in order to obtain high water absorbing and quick-drying properties, and has hydrophilicity. An example of extendable fiber comprising a hydrophilic agent is extendable fiber formed by mixing a hydrophilic agent with an extendable fiber material and then spinning it, also referred to as hydrophilic agent-kneaded fiber.

The nonwoven fabric comprising extendable fiber and elastic fiber in accordance with an embodiment of the disclosure may be coated with a hydrophilic agent, and the distribution of the coated hydrophilic agent in the nonwoven fabric comprising extendable fiber and elastic fiber is not particularly restricted so long as the nonwoven fabric comprising extendable fiber and elastic fiber has the prescribed water absorbing property and quick-drying property. For example, when the hydrophilic agent has been coated onto a nonwoven fabric by a dip coating method, it is common for the hydrophilic agent to be distributed throughout the entire nonwoven fabric, or more specifically, the surface of each fiber is covered with the hydrophilic agent, and when the hydrophilic agent has been coated onto a nonwoven fabric by a spray coating method it is common for the hydrophilic agent to be abundantly distributed on the surface of the nonwoven fabric, or when the hydrophilic agent has been coated on a nonwoven fabric by a bar coating method, it is common for the hydrophilic agent to be more abundantly distributed on the protrusions than in the recesses of the coated surface.

Hydrophilic agents that can be used to coat nonwoven fabrics, and hydrophilic agents that can be used to coat extendable fiber and elastic fiber, may be applied without any particular restrictions so long as they are commonly employed as hydrophilic agents in the technical field, and examples include anionic hydrophilic agents, cationic hydrophilic agents, nonionic hydrophilic agents, and combinations thereof, with nonionic hydrophilic agents being preferred for their high heat resistance.

When the nonwoven fabric is to be coated with the hydrophilic agent, the amount of hydrophilic agent is preferably coated at a basis weight of about 0.01-0.5 $g/m^2$ on the nonwoven fabric, and it is coated at a basis weight of more preferably about 0.03-0.3 $g/m^2$ and even more preferably about 0.05-0.1 $g/m^2$. A basis weight of below about 0.01 $g/m^2$ will tend to result in insufficient hydrophilicity, a high water contact angle and insufficient water absorbing and quick-drying properties, while a basis weight of greater than about 0.5 $g/m^2$ will tend to result in anchoring of elastic fiber and extendable fiber by the hydrophilic agent, and reduced elasticity and flexibility.

When the extendable fiber and elastic fiber contain a hydrophilic agent, the amount of hydrophilic agent is preferably about 0.05-10.0 mass %, more preferably about 0.1-7.0 mass % and even more preferably about 0.2-5.0 mass %, based on the mass of the fiber. A ratio of less than about 0.05 mass % will tend to result in insufficient hydrophilicity, a high water contact angle and insufficient water absorbing and quick-drying properties, while a ratio of greater than about 10.0 mass % may lower the physical properties of the extendable fiber and elastic fiber.

In the nonwoven fabric comprising extendable fiber and elastic fiber 1, as shown in FIG. 1, the protrusions 3 and recesses 4 are each parallel to the first direction A, and arranged in an alternating manner in the direction perpendicular to the first direction A. However, there are no particular restrictions on the pattern of the plurality of protrusions and plurality of recesses on the first side of the nonwoven fabric comprising extendable fiber and elastic fiber in accordance with another embodiment of the disclosure, and the nonwoven fabric comprising extendable fiber and elastic fiber may have the plurality of protrusions and plurality of recesses on the first side in a predetermined pattern, formed by the method described below.

FIG. 1 shows an embodiment wherein the second side on the side opposite the first side is flat, but in accordance with another embodiment of the disclosure, irregularities may be present on the second side (this will be explained in greater detail in relation to FIG. 2).

When the second side is flat, the second side will have more excellent adhesion when bonded to another nonwoven fabric.

FIG. 1 also shows an embodiment wherein the extendable fiber EX is oriented along the first direction A on the protrusions 3, but the extendable fiber in the nonwoven fabric comprising extendable fiber and elastic fiber in accordance with another embodiment of the disclosure is not oriented.

Figure 2:
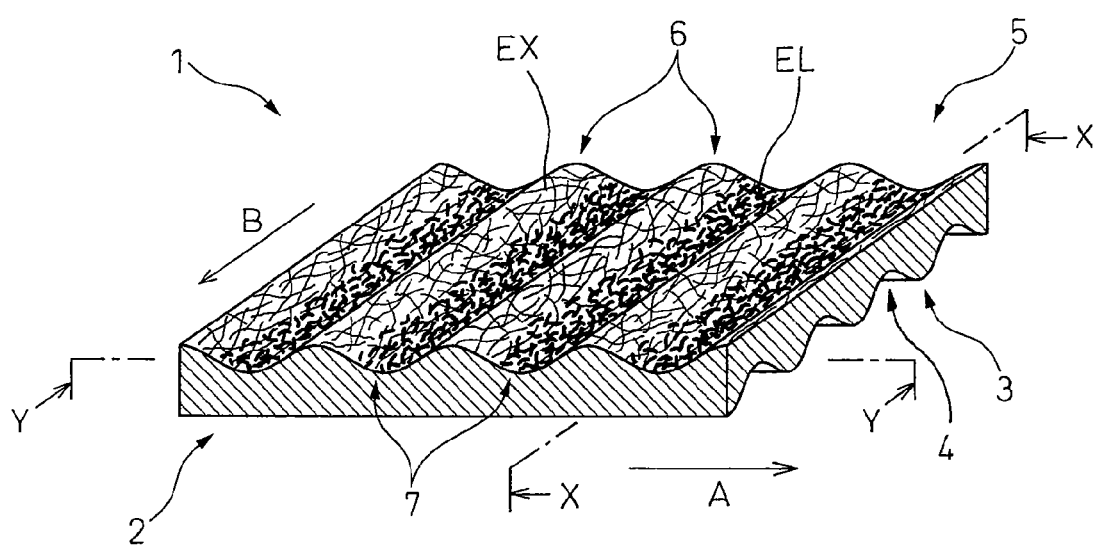
FIG. 2 is a schematic view of a nonwoven fabric comprising extendable fiber and elastic fiber in accordance with another embodiment of the disclosure.

FIG. 2 is a schematic view of the nonwoven fabric comprising extendable fiber and elastic fiber in accordance with another embodiment of the disclosure. The nonwoven fabric comprising extendable fiber and elastic fiber 1, shown in FIG. 2, has a second side 5 on the side opposite the first side 2, and the second side 5 has a plurality of protrusions 6 and a plurality of recesses 7. In the embodiment shown in FIG. 2, the first side 2 is identical to the first side 2 shown in FIG. 1.

The hydrophilic agent is not shown in FIG. 2.

In the nonwoven fabric comprising extendable fiber and elastic fiber 1 shown in FIG. 2, the protrusions 6 are rich in extendable fiber EX while the recesses 7 are rich in elastic fiber EL, and the proportion of extendable fiber in the protrusions 6 is greater than the proportion of extendable fiber in the recesses V. Also, in the nonwoven fabric comprising extendable fiber and elastic fiber 1 shown in FIG. 2, the protrusions 6 and the recesses 7 are both parallel to the second direction B, and are alternately situated in the direction perpendicular to the second direction B. Also, the first direction A and second direction B are perpendicular in the nonwoven fabric comprising extendable fiber and elastic fiber 1 shown in FIG. 2. In the embodiment shown in FIG. 2, the extendable fiber EX in the protrusions 6 and the elastic fiber EL in the recesses 7 are not oriented.

A nonwoven fabric comprising extendable fiber and elastic fiber, such as shown in FIG. 2 has a proportion of extendable fiber in the protrusions on the second side that is higher than the proportion of extendable fiber in the recesses on the second side, and it therefore exhibits excellent feel on the skin and excellent elasticity, similar to the first side.

From the viewpoint of the effect of the disclosure, and especially both the feel on the skin and elasticity, the proportion of extendable fiber in the protrusions on the second side is preferably at least 2 mass % higher, more preferably at least 4 mass % higher, even more preferably at least 6 mass % higher and yet more preferably at least 8 mass % higher than the proportion of extendable fiber in the recesses on the second side.

The proportion of extendable fiber on the second side may be evaluated by a solvent method or dyeing method, similar to the first side.

The nonwoven fabric comprising extendable fiber and elastic fiber shown in FIG. 2 also has recesses with small thicknesses and low aeration resistance in the thickness direction on the first side and second side, and therefore exhibits excellent air permeability in the thickness direction of the nonwoven fabric, while the recesses that serve as passageways for air in the planar direction are also present on the first side and second side, and therefore the air permeability is excellent in the planar direction, and especially the first direction and second direction, of the nonwoven fabric.

In the nonwoven fabric comprising extendable fiber and elastic fiber 1, as shown in FIG. 2, the plurality of protrusions 3 and plurality of recesses 4 are each parallel to the first direction A, and arranged in an alternating manner in the direction perpendicular to the first direction A, but there are no particular restrictions on the pattern of the plurality of protrusions and plurality of recesses on the first side of the nonwoven fabric comprising extendable fiber and elastic fiber in accordance with another embodiment of the disclosure.

Also, in the nonwoven fabric comprising extendable fiber and elastic fiber 1, as shown in FIG. 2, the protrusions 6 and recesses 7 are each parallel to the second direction B, and arranged in an alternating manner in the direction perpendicular to the second direction B. However, there are no particular restrictions on the pattern of the plurality of protrusions and plurality of recesses on the second side of the nonwoven fabric comprising extendable fiber and elastic fiber according another embodiment of the disclosure, and the nonwoven fabric of comprising extendable fiber and elastic fiber may have the plurality of protrusions and plurality of recesses on the second side in a predetermined pattern, formed by the method described below.

Furthermore, while there is no particular orientation of the extendable fiber EX in the protrusions 6 or the orientation of the elastic fiber EL in the recesses 7 in the embodiment shown in FIG. 2, there is no limitation to this in the nonwoven fabric comprising extendable fiber and elastic fiber in accordance with another embodiment of the disclosure, and the extendable fiber EX in the protrusions 6 may have an orientation along the second direction B, and/or the elastic fiber EL in the recesses 7 may have an orientation along the second direction B.

Also, the first direction A and second direction B are perpendicular in the nonwoven fabric comprising extendable fiber and elastic fiber 1 shown in FIG. 2, but there is no restriction to this relationship between the first direction and second direction, and the first direction and second direction may have any desired angle between them. For example, the first direction and second direction may be parallel, or in other words, the angle between them may be 0°. In accordance with such an embodiment, the elasticity is excellent in the direction perpendicular to the first direction (and the second direction), and the air permeability is excellent in the planar direction, and especially the first direction (and second direction).

The nonwoven fabric comprising extendable fiber and elastic fiber in accordance with an embodiment of the disclosure preferably has the first direction and second direction perpendicular to each other. In addition, the nonwoven fabric comprising extendable fiber and elastic fiber according an embodiment of the disclosure more preferably has the first direction as the direction of transport (hereunder also referred to as "machine direction MD") and the second direction as the cross-machine direction perpendicular to the machine direction (hereunder, the cross-machine direction perpendicular to the machine direction will also be referred to simply as "cross-machine direction" or "cross-machine direction CD").

Figure 3:
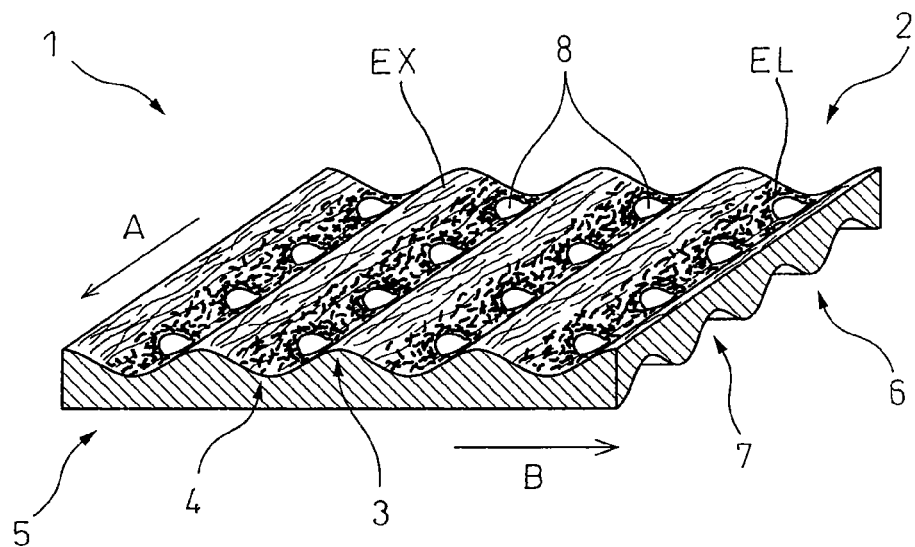
FIG. 3 is a schematic view of a nonwoven fabric comprising extendable fiber and elastic fiber in accordance with yet another embodiment of the disclosure.
Figure 4:
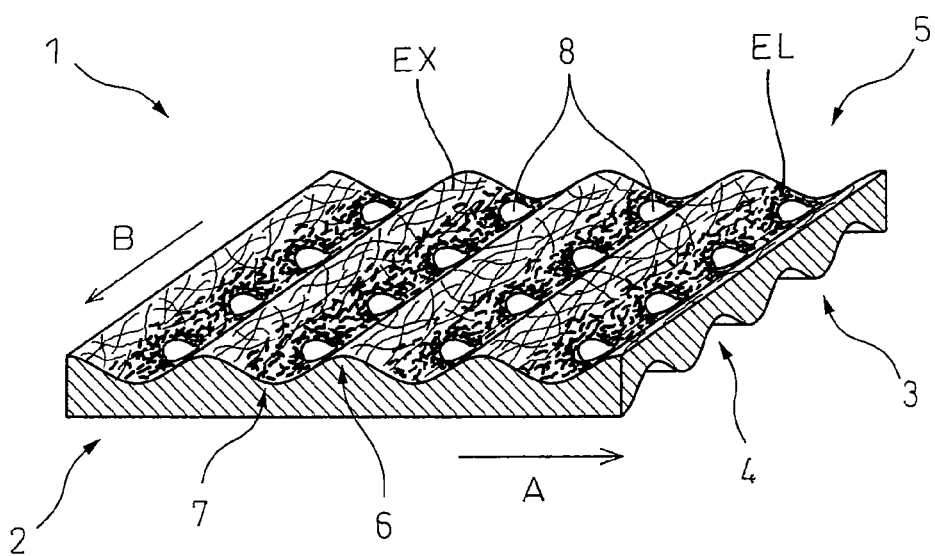
FIG. 4 is a schematic view of a nonwoven fabric comprising extendable fiber and elastic fiber in accordance with yet another embodiment of the disclosure.

FIG. 3 and FIG. 4 are schematic views of the nonwoven fabric comprising extendable fiber and elastic fiber in accordance with other embodiments of the disclosure. The nonwoven fabric comprising extendable fiber and elastic fiber 1, shown in FIG. 3 and FIG. 4, each have a first side 2, and the first side 2 has protrusions 3 and recesses 4 each parallel to the first direction A, that are alternating in the direction perpendicular to the first direction A, while the second side 5 has protrusions 6 and recesses 7 each parallel to the second direction B, that are alternating in the direction perpendicular to the second direction B. The nonwoven fabric comprising extendable fiber and elastic fiber 1, shown in FIG. 3, also has open holes 8 that connect the recesses 4 and recesses 7.

The hydrophilic agent is not shown in FIG. 3 or FIG. 4.

On the first side 2 of the nonwoven fabric comprising extendable fiber and elastic fiber 1 shown in FIG. 3, the protrusions 3 are rich in extendable fiber EX while the recesses 4 are rich in elastic fiber EL, and therefore the proportion of extendable fiber in the protrusions 3 is greater than the proportion of extendable fiber in the recesses 4. In the protrusions 3, the extendable fiber EX tends to be situated along the first direction A.

On the second side 5 of the nonwoven fabric comprising extendable fiber and elastic fiber 1 shown in FIG. 4, the protrusions 6 are rich in extendable fiber EX while the recesses 7 are rich in elastic fiber EL, and therefore the proportion of extendable fiber in the protrusions 6 is greater than the proportion of extendable fiber in the recesses 7.

Also, the elastic fiber EL is situated surrounding the open holes 8 in the recesses 4 and recesses 7 in FIG. 3 and FIG. 4.

Because the nonwoven fabric comprising extendable fiber and elastic fiber shown in FIG. 3 and FIG. 4 has recesses with small thicknesses and low aeration resistance in the thickness direction on the first side and second side, while having one or a plurality of open holes with aeration resistance of about 0 in the thickness direction, it exhibits particularly excellent air permeability in the thickness direction of the nonwoven fabric, while the recesses that serve as passageways for air in the planar direction are also present on the first side and second side, and therefore the air permeability is excellent in the planar direction, and especially the first direction and second direction, of the nonwoven fabric. Also, the nonwoven fabric comprising extendable fiber and elastic fiber in accordance with an embodiment of the disclosure, such as shown in FIG. 3 and FIG. 4 has open holes that can change their structure during stretching, and therefore the strength is low during initial stretching and the fabric can easily follow movement of the body.

In FIG. 3, the protrusions 3 and recesses 4 on the first side and the protrusions 6 and recesses 7 on the second side are oriented in specific directions, but their directions and orientations are not particularly restricted for the nonwoven fabric comprising extendable fiber and elastic fiber in accordance with another embodiment of the disclosure. The orientation of the extendable fiber and elastic fiber may also be as desired, and the extendable fiber and/or elastic fiber in the plurality of protrusions on the first side, the plurality of recesses on the first side, the plurality of protrusions on the second side and/or the plurality of recesses on the second side may be oriented or non-oriented.

Figure 5:
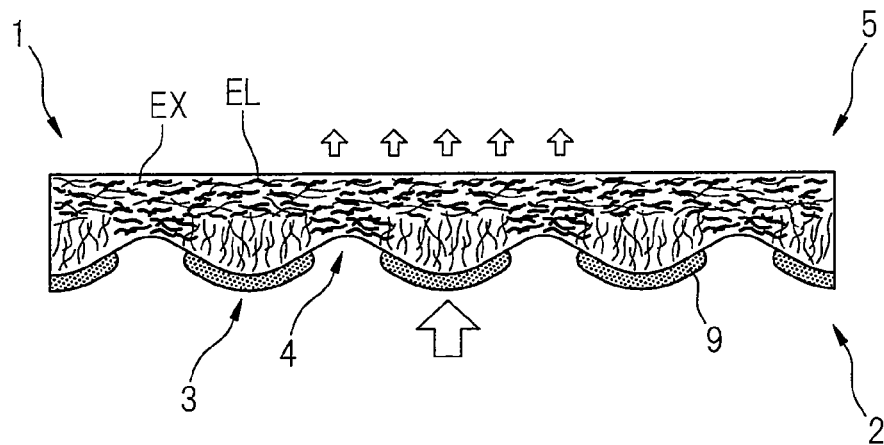
FIG. 5 is a schematic view of a nonwoven fabric comprising extendable fiber and elastic fiber in accordance with an embodiment of the disclosure, from cross-section X-X in FIG. 1.

FIG. 5 is a schematic view of a nonwoven fabric comprising extendable fiber and elastic fiber 1, along cross-section X-X of FIG. 1. In FIG. 5, the first side of the nonwoven fabric comprising extendable fiber and elastic fiber is shown facing downward, in order to illustrate absorption of moisture from the first side. Also, FIG. 5 shows an embodiment where the protrusions on the first side 3 are coated with a hydrophilic agent 9, as an embodiment of the nonwoven fabric comprising extendable fiber and elastic fiber of the disclosure.

The reason for the high water absorbing property and quick-drying property of the nonwoven fabric comprising extendable fiber and elastic fiber of the disclosure is as follows.

In a nonwoven fabric comprising extendable fiber and elastic fiber 1, the protrusions 3 on the first side 2, which have been hydrophilized by coating with the hydrophilic agent 9, are able to rapidly take up moisture when the protrusions 3 contact with moisture. Since the protrusions 3 have a high proportion of extendable fiber EX that has been hydrophilized with the hydrophilic agent, they are able to rapidly take up moisture.

In the protrusions 3, the extendable fiber EX which is oriented in the thickness direction of the nonwoven fabric 1 then rapidly sends the absorbed moisture to the second side 5. Since each fiber extends in the planar direction on the second side 5, the absorbed liquid can rapidly diffuse in the planar direction. The liquid that has diffused in the planar direction presumably allows rapid volatilization of moisture from the entire second side. Furthermore, since protrusions 3 are formed on the first side, the formation of protrusions 3 in the nonwoven fabric comprising extendable fiber and elastic fiber 1 results in density in the relationship: density near first side<density near second side, and more specifically, the density is in the relationship: density near protrusions 3<density near recesses 4<density near second side 5, and it is for this reason that the moisture on the second side can be rapidly drawn up by capillary movement.

To concisely summarize the above, moisture is absorbed through the protrusions 3, moves rapidly to the second side 5 and diffuses throughout the entire second side 5, allowing rapid volatilization, as indicated by the arrows in FIG. 5.

In accordance with the embodiment illustrated in FIG. 2, moisture is absorbed through the protrusions 3, rapidly moves to the second side 5 and can rapidly volatilize through the second side 5, which has protrusions 6 and recesses 7 and a larger surface area than the flat fabric illustrated in FIG. 1.

Figure 6:
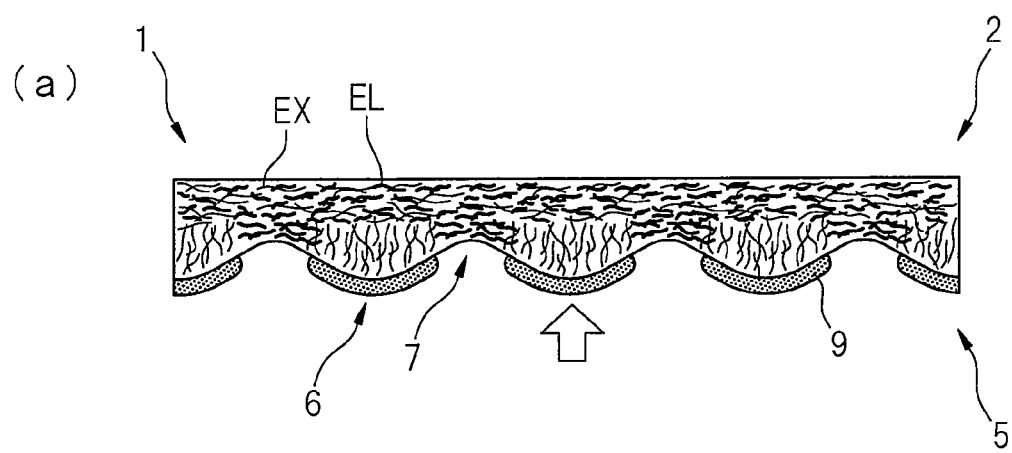
FIGS. 6 (*a*) and 6 (*b*) are schematic views of a nonwoven fabric comprising extendable fiber and elastic fiber in accordance with an embodiment of the disclosure, from cross-section X-X and cross-section Y-Y in FIG. 2.
Figure 6:
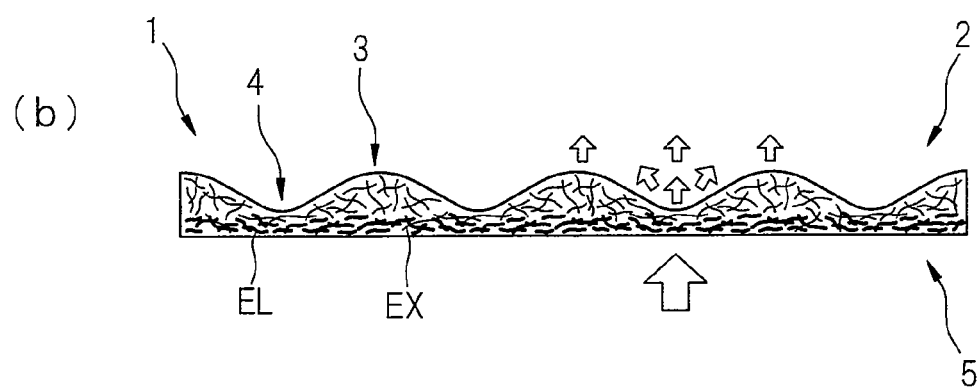

FIG. 6 is a schematic view of a nonwoven fabric comprising extendable fiber and elastic fiber 1, from cross-section X-X and cross-section Y-Y in FIG. 2. FIG. 6[a] and [b] show cross-section Y-Y and cross-section X-X. In FIG. 6, the second side of the nonwoven fabric comprising extendable fiber and elastic fiber is shown facing downward, in order to illustrate absorption of moisture from the second side. Also, FIG. 6 shows an embodiment where the protrusions on the first side 3 are coated with a hydrophilic agent 9, as an embodiment of the nonwoven fabric comprising extendable fiber and elastic fiber of the disclosure.

In a nonwoven fabric comprising extendable fiber and elastic fiber 1, as shown in FIG. 6[a], the protrusions 6 on the second side 5, which have been hydrophilized by coating with the hydrophilic agent 9, are able to rapidly take up moisture when the protrusions 6 contact with moisture. Since the protrusions 6 have a high proportion of extendable fiber EX that has been hydrophilized with the hydrophilic agent, they are able to rapidly take up moisture.

As shown in FIG. 6[b], the moisture absorbed through the protrusions 6 of the second side 5 can then be volatilized through the protrusions 3 and recesses 4 of the first side 2, but since the recesses 4 are the sections of low nonwoven fabric thickness, the absorbed moisture can rapidly volatilize off through the recesses 4.

To concisely summarize the above, moisture that has been rapidly absorbed through the protrusions 6 can rapidly volatilize off primarily through the recesses 4, as shown by the arrows in FIG. 6[b]. The first side 2 which has protrusions 3 and recesses 4 contributes to rapid volatilization by its large surface area.

The nonwoven fabric comprising extendable fiber and elastic fiber of in accordance with an embodiment the disclosure has a water absorbing property represented by a water absorption height of 10 mm or greater in a water absorption test, where the water absorption test is conducted in accordance with JIS L 1907:2010, "Water absorption test methods for fiber products", 7.1.2 Byreck method, with an immersion time of 5 minutes.

The nonwoven fabric comprising extendable fiber and elastic fiber in accordance with an embodiment of the disclosure has a water absorbing property represented by a water absorption height of 10 mm or greater in a water absorption test, and preferably it has a water absorbing property represented by a water absorption height of preferably about 15 mm or greater and more preferably a water absorption height of about 20 mm or greater. Since the water absorption height is an indicator of the degree of the water absorbing property of a nonwoven fabric, a higher height is preferred.

The nonwoven fabric comprising extendable fiber and elastic fiber in accordance with an embodiment of the disclosure has a quick-drying property represented by a transpiration rate of 20 mass % or greater in a transpiration test, where the transpiration test may be carried out as follows.

(1) A 1 mL portion of physiological saline is added dropwise to a watch glass with a diameter of 105 mm, in a thermostatic chamber at 20° C., 60% RH.

(2) A sample with a size of 100 mm×100 mm is provided.

(3) The total mass W of the watch glass and the sample is measured.

(4) The total mass $W_0$ of the watch glass, the physiological saline (1 mL) and the sample is measured.

(5) The sample is placed in the watch glass and contacted with 1 mL of physiological saline.

(6) After 2 hours, the total mass $W_t$ of the watch glass, the physiological saline (1 mL) and the sample is measured.

(7) The transpiration rate after 2 hours is measured based on the following formula (1).

$$\text{Transpiration rate (\%)} = 100 \times (W_0 - W_t)/(W_0 - W)$$

The nonwoven fabric comprising extendable fiber and elastic fiber in accordance with an embodiment of the disclosure has a quick-drying property represented by a transpiration rate of 20 mass % or greater in a transpiration test, and preferably it has a quick-drying property represented by a transpiration rate of about 30 mass % or greater and more preferably a transpiration rate of about 40 mass % or greater. Since the transpiration rate is an indicator of the quick-drying property of the nonwoven fabric, a larger value is preferred.

[Method for Producing Nonwoven Fabric Comprising Extendable Fiber and Elastic Fiber]

The method for producing a nonwoven fabric comprising extendable fiber and elastic fiber in accordance with the disclosure comprises a step of providing a nonwoven fabric to be treated which comprises extendable fiber and elastic fiber.

As used herein, a "nonwoven fabric to be treated which comprises extendable fiber and elastic fiber" refers to a nonwoven fabric starting material, i.e. the nonwoven fabric before treatment, and it differs from a nonwoven fabric with high water absorbing and quick-drying properties after being subjected to the non-homogeneous stretching step and fluid treatment step described below.

The nonwoven fabric to be treated which comprises extendable fiber and elastic fiber is not particularly restricted so long as it is a nonwoven fabric comprising the aforementioned extendable fiber and elastic fiber, and for example, it may be a nonwoven fabric produced by any known method, such as an air-through nonwoven fabric, spunbond nonwoven fabric, point bond nonwoven fabric, spunlace nonwoven fabric, airlaid nonwoven fabric or meltblown nonwoven fabric, or a nanofiber-containing nonwoven fabric.

The extendable fiber and elastic fiber can be selected from among these fibers, and the fiber diameter of the extendable fiber is preferably selected in consideration of thinning of the fiber diameter in subsequent steps.

The fiber lengths of the fibers are not particularly restricted, and there may be mentioned staple fibers and continuous filaments, for example. When two or more fibers are mixed, the fiber lengths of the fibers may be the same or different.

The method of the disclosure comprises a step of non-homogeneous stretching of the nonwoven fabric to be treated which comprises extendable fiber and elastic fiber, to form a nonwoven fabric with high-stretch regions and low-stretch regions (this will hereunder also be referred to as "non-homogeneous stretching step").

The non-homogeneous stretching step is carried out in the nonwoven fabric to be treated which comprises the extendable fiber and elastic fiber partially (i) to destroy the points of fiber contact in the nonwoven fabric and create a partial web state of the anchored fibers, and/or (ii) to form stretched extendable fiber between the points of fiber contact in the nonwoven fabric. The stretched extendable fiber easily moves when treated with a fluid, and therefore irregularities are easily formed in the nonwoven fabric.

Since the elastic fiber has a higher elastic limit than the stress applied during the non-homogeneous stretching step, the elastic fiber that has been temporarily stretched during the non-homogeneous stretching step can subsequently return to its original length.

The points of contact may be heat sealing points, in the case of an air-through nonwoven fabric, or they may be thermocompression bonding points in the case of a spunbond nonwoven fabric or point bond nonwoven fabric, or fiber tangling points in the case of a spunlace nonwoven fabric.

As used herein, "high-stretch region" means a region that has been stretched so that the degree of stretch of the stretched extendable fiber is higher than in the low-stretch regions, while "low-stretch region" means a region that has been stretched so that the degree of stretch of the stretched extendable fiber is lower than in the high-stretch regions, and it includes regions in which no stretched extendable fiber has been formed, i.e. unstretched regions.

Also as used herein, the term "non-homogeneous stretching" refers to stretching so as to form a nonwoven fabric having high-stretch regions and low-stretch regions, or in other words, stretching so as to form a nonwoven fabric having different degrees of stretching of the stretched extendable fiber, depending on the location.

The non-homogeneous stretching step is not particularly restricted so long as it allows formation of a nonwoven fabric with high-stretch regions and low-stretch regions, and it may be carried out by any desired means, such as passing the nonwoven fabric to be treated which comprises extendable fiber and elastic fiber, through the gap between a pair of gear rolls each having a rotational axis line perpendicular to the machine direction and rotating while engaging the plurality of teeth arranged around the peripheral surface of each gear roll (this will hereunder also be referred to as "gear stretching").

Figure 7:
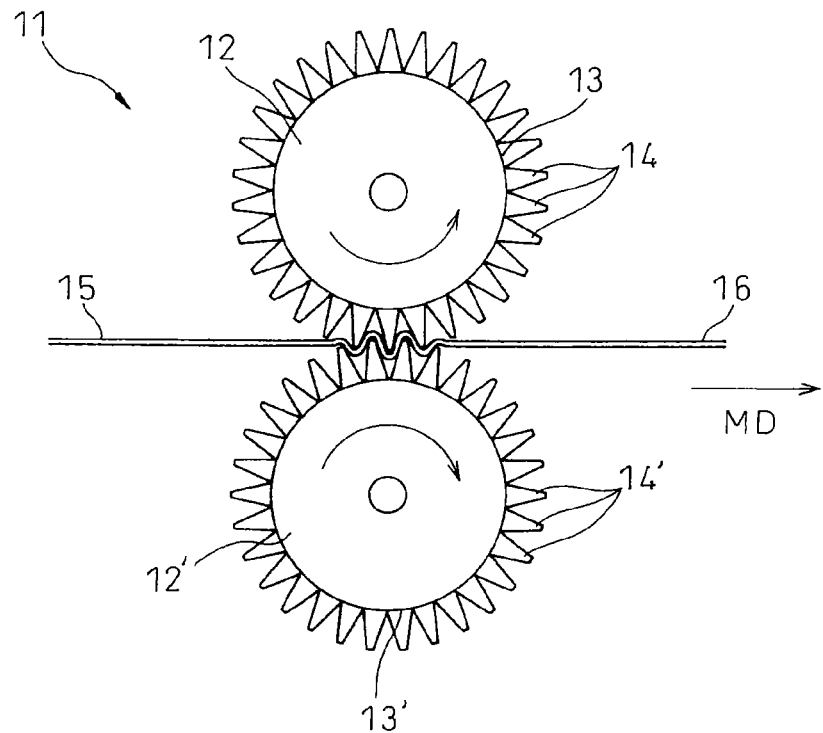
FIG. 7 is a schematic view that shows gear stretching.

FIG. 7 is a schematic view that shows gear stretching. The gear stretcher 11 shown in FIG. 7 has a pair of gear rolls 12 and 12'. A plurality of teeth 14 and 14' are arranged around the peripheral surfaces 13 and 13' of the gear rolls 12 and 12'. In the gear stretcher 11 shown in FIG. 7, the rotational axis lines of the gear rolls 12 and 12' are both perpendicular to the machine direction MD of the nonwoven fabric. The plurality of teeth 14 and 14' are arranged on the peripheral surfaces 13 and 13' in a manner parallel to the rotational axis lines.

In the gear stretcher 11 shown in FIG. 7, the nonwoven fabric to be treated which comprises extendable fiber and elastic fiber 15 is passed through the roll gap between the pair of gear rolls 12 and 12', and when it passes through the gear rolls 12 and 12', the nonwoven fabric to be treated which comprises extendable fiber and elastic fiber 15 is stretched by the mutually engaging plurality of teeth 14 and 14' of the gear rolls 12 and 12', on the three-point bending principle, to form a nonwoven fabric 16 having high-stretch regions and low-stretch regions. The nonwoven fabric 16 having high-stretch regions and low-stretch regions has alternating high-stretch regions and low-stretch regions in the machine direction MD, which are parallel to the cross-machine direction.

In the nonwoven fabric to be treated which comprises extendable fiber and elastic fiber 15, the fabric of the nonwoven fabric is anchored in the regions that are in contact with the tips of the plurality of teeth 14 and 14', and therefore undergoes little or no stretching, forming the low-stretch regions. On the other hand, the regions of the nonwoven fabric to be treated which comprises extendable fiber and elastic fiber 15 that do not contact the tips of the plurality of teeth 14 and 14', i.e. the regions between the tips of the teeth 14 and the tips of the teeth 14', are widely stretched to form high-stretch regions.

Figure 8:
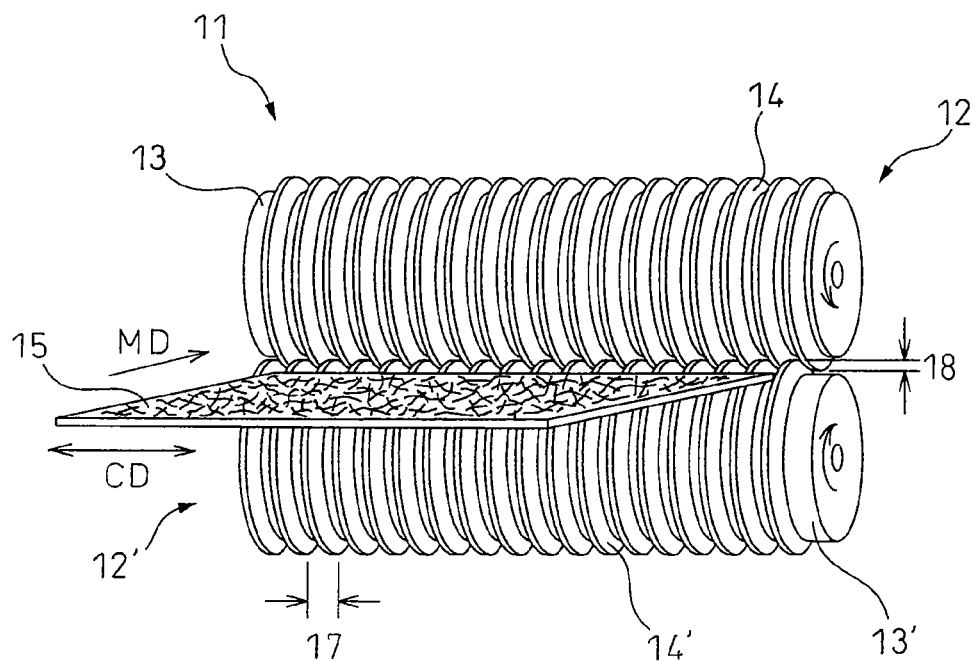
FIG. 8 is a schematic view that shows gear stretching.

Gear stretching can also be accomplished using a gear stretcher as shown in FIG. 8.

FIG. 8 is a schematic view that shows gear stretching. The gear stretcher 11 shown in FIG. 8 has a pair of gear rolls 12 and 12'. A plurality of teeth 14 and 14' are arranged around the peripheral surfaces 13 and 13' of the gear rolls 12 and 12'. In the gear stretcher 11 shown in FIG. 8, the plurality of teeth 14 and 14' are arranged on the respective peripheral surfaces 13 and 13' in a manner perpendicular to the rotational axis lines of the gear rolls 12 and 12'. When the plurality of teeth 14 and 14' are arranged perpendicular to the rotational axis lines in this manner, it is possible to form a nonwoven fabric having parallel high-stretch regions and low-stretch regions, each parallel to the machine direction MD, alternating in the cross-machine direction CD.

Figure 9:
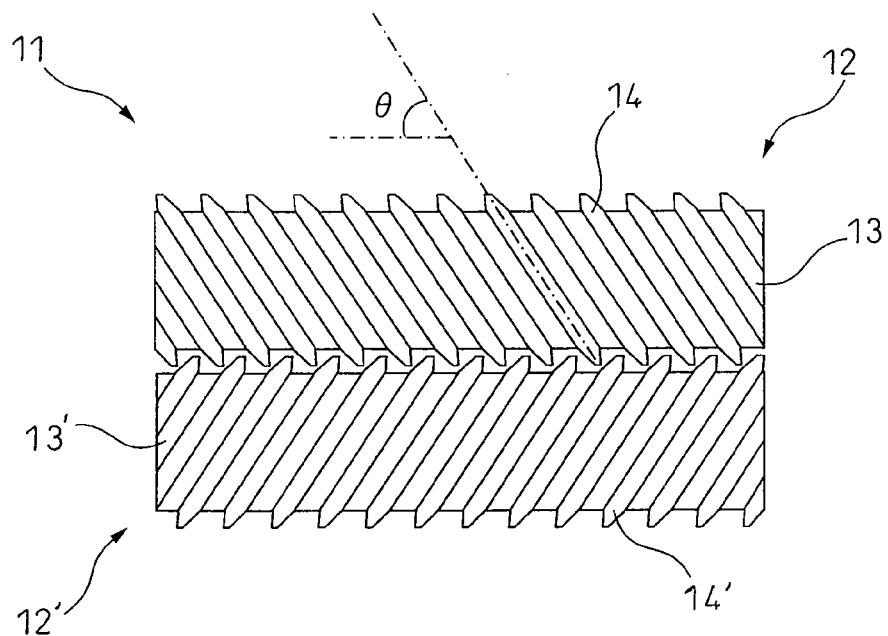
FIG. 9 is a schematic view that shows gear stretching.

The gear stretching may also be accomplished using a gear stretcher having a plurality of teeth arranged around the peripheral surfaces of gear rolls, and slanted with respect to the rotational axis lines of the gear rolls, as shown in FIG. 9. FIG. 9 is a schematic view that shows gear stretching. The gear stretcher 11 shown in FIG. 9 has a pair of gear rolls 12 and 12', with a plurality of teeth 14, 14' arranged around the peripheral surfaces 13, 13' of the gear rolls 12, 12'. In the gear stretcher 11 shown in FIG. 9, the rotational axis lines of the gear rolls 12 and 12' are both perpendicular to the machine direction MD of the nonwoven fabric. The plurality of teeth 14 and 14' are arranged around the peripheral surfaces 13 and 13' at a fixed angle of θ with respect to the rotational axis line.

In the gear stretcher shown in FIG. 9, one tooth 14 and one tooth 14' may be situated on the peripheral surfaces 13 and 13' of the gear rolls 12 and 12', depending on the angle of θ and the gear pitch.

The gear stretcher may be appropriately selected depending on the desired performance for the nonwoven fabric to be formed.

When high elasticity is required, the nonwoven fabric to be treated which comprises extendable fiber and elastic fiber may be subjected to stretching several times using a gear stretcher, such as shown in FIG. 7 to FIG. 9.

In these gear stretchers, the gear pitch is preferably about 1-10 mm and more preferably about 2-6 mm. If the gear pitch is less than about 1 mm it may be necessary to reduce the thickness of the gear blades and portions of the nonwoven fabric may become severed, while if the gear pitch is greater than about 10 mm, the stretch ratio may be reduced and it may become difficult for the extendable fiber to be stretched.

The gear pitch is the interval between one tooth and another tooth, and it is denoted by numeral 17 in FIG. 8.

In this gear stretcher, the gear tooth cutting depth is preferably about 0.5 mm or greater. If the gear tooth cutting depth is less than about 0.5 mm, the nonwoven fabric stretching may be inadequate and the extendable fiber may be difficult to stretch.

The gear tooth cutting depth is the depth at the section where the top gear roll tooth and bottom gear roll tooth overlap, and it is denoted by numeral 18 in FIG. 8.

In a nonwoven fabric having high-stretch regions and low-stretch regions, the stretch ratio for each gear stretching is preferably about 30-400% and more preferably about 50-200%. If the stretch ratio is lower than about 30% the extendable fiber may not be stretched, and if the stretch ratio is higher than about 400%, the strength of the nonwoven fabric with high-stretch regions and low-stretch regions will tend to be weakened and the extended extendable fiber will tend to be shed preferentially, often causing transport problems, and/or the extendable fiber may undergo breakage.

Throughout the present specification, the term "stretch ratio" refers to the value calculated by the following formula:

$$\text{Stretch ratio (\%)} = 100 \times \left[ \frac{\sqrt{P^2 + 4D^2}}{P} - 1 \right]$$

where P is the gear pitch and D is the gear tooth cutting depth.

The reel-off speed of the nonwoven fabric to be treated which comprises extendable fiber and elastic fiber will vary depending on the desired stretch ratio, but it may be about 10 m/min or greater, for example. The take-up speed of the nonwoven fabric having alternating high-stretch regions and low-stretch regions will vary depending on the stretch ratio, etc., and when the nonwoven fabric to be treated which comprises extendable fiber and elastic fiber has been stretched in the machine direction, the value of the stretch ratio on the reel-off speed serves as a measure of the take-up speed.

The method of the disclosure comprises a step of coating a hydrophilic agent-containing solution onto the nonwoven fabric with the high-stretch regions and low-stretch regions (hereunder also referred to as "hydrophilic agent-coating step").

There are no particular restrictions on the method of coating the hydrophilic agent-containing solution onto the nonwoven fabric with high-stretch regions and low-stretch regions that has been formed in the non-homogeneous stretching step, and examples include spray coating methods, curtain coating methods, dip coating methods, bar coating methods, roll coating methods and spin coating methods.

The hydrophilic agent-coating step may be carried out on a support and followed directly by a fluid treatment step. For example, the hydrophilic agent-coating step may be carried out by spraying the hydrophilic agent solution onto a nonwoven fabric with high-stretch regions and low-stretch regions situated on a support.

The hydrophilic agent-containing solution may be one comprising the hydrophilic agent dissolved in a solvent, for example, an organic solvent, such as ethanol or methyl ethyl ketone, or water, with water being preferred for high safety.

The solvent may be one with a relatively high boiling point. The hydrophilic agent-coating step is followed by a fluid treatment step with spraying hot air or the like, and therefore the solvent is easily volatilized off.

The method of the disclosure comprises a step of placing the nonwoven fabric with high-stretch regions and low-stretch regions on which the hydrophilic agent has been coated on a support and spaying a fluid thereon, to form the nonwoven fabric comprising extendable fiber and elastic fiber (this will hereunder also be referred to as "fluid treatment step").

At least a portion of the web fiber and/or stretched extendable fiber present in the high-stretch regions, formed in the non-homogeneous stretching step, is impacted with the sprayed fluid on the side impacting with the fluid (hereunder referred to as "fluid-impacting side"), and is then rebounded and separated out in a planar direction, such as the cross-machine direction. More specifically, the stretched extendable fiber in the sections blasted with the sprayed fluid moves elsewhere, with mainly the elastic fiber remaining, so that a plurality of recesses are formed on the first side.

The elastic fiber is subjected to the force of the fluid impact, but since it stops with stress at less than the elastic limit, it usually returns to its original location after the fluid has been sprayed. Therefore, although the plurality of recesses on the first side are rich in elastic fiber, the compactness of the fiber is low. The stretched extendable fiber forms protrusions on both sides of the plurality of recesses on the first side. Consequently, the plurality of protrusions on the first side are rich in extendable fiber and the separated extendable fiber becomes compact, thus increasing the fiber compactness. In some cases, the fluid-impacting side corresponds to the first side of the nonwoven fabric comprising extendable fiber and elastic fiber, and the direction of the trajectory through which the fluid is blasted corresponds to the first direction.

Also, on the side opposite the fluid-impacting side (hereunder referred to as "non-fluid-impacting side", corresponding to the second side), at least a portion of the web fiber and/or stretched extendable fiber moves along the flow of the fluid passing through the nonwoven fabric.

The fluid used in the fluid treatment step may be air, such as heated air, or water vapor, or water, such as hot water.

The fluid may be blasted from an anchored fluid nozzle onto the nonwoven fabric having high-stretch regions and low-stretch regions, which has been coated with the hydrophilic agent, or it may be blasted from a fluid nozzle that is reciprocating in the cross-machine direction. The fluid may also be continuously or intermittently blasted from a fluid nozzle onto the nonwoven fabric having high-stretch regions and low-stretch regions, which has been coated with the hydrophilic agent. These may also be used in combination to form a plurality of protrusions and a plurality of recesses on the first side, having different patterns including a predetermined pattern.

The fluid may be appropriately selected depending on the form of the nonwoven fabric having high-stretch regions and low-stretch regions, which has been coated with the hydrophilic agent. For example, for treatment of a nonwoven fabric with a low gear pitch and a large stretch ratio, air or water vapor is preferably selected as the fluid as this will allow movement of primarily the stretched extendable fiber with relatively low energy. Furthermore, since the joining points between fibers are increased in number when using a nonwoven fabric with a large gear pitch and many low-stretch regions, a relatively high energy is necessary for movement of the stretched extendable fiber, and therefore water or water vapor is preferably selected as the fluid, with water vapor being more preferred. This is because moisture does not easily remain in the sections with a large composite fiber content and the joining points between the sections with a high composite fiber content are not usually destroyed, so that the stretched extendable fibers in the sections that are to undergo movement can be easily moved.

The fluid treatment step can be carried out by a known method using an apparatus known in the technical field.

In the method in accordance with an embodiment of the disclosure, the support used to support the nonwoven fabric with high-stretch regions and low-stretch regions may be a support commonly used in the technical field, such as a metal or plastic conveyor net, or a paper making web. The support will usually be one with fluid permeability.

In the method in accordance with a different embodiment of the disclosure, a support having protrusions and depressions may be used for further improved air permeability, feel on the skin (for example, low contact area) and liquid uptake properties of the nonwoven fabric.

As used herein, a "protrusion" is a section used to form a plurality of recesses on the second side of the nonwoven fabric, and a "depression" is a section used to form a plurality of protrusions on the second side of the nonwoven fabric.

Figure 10:
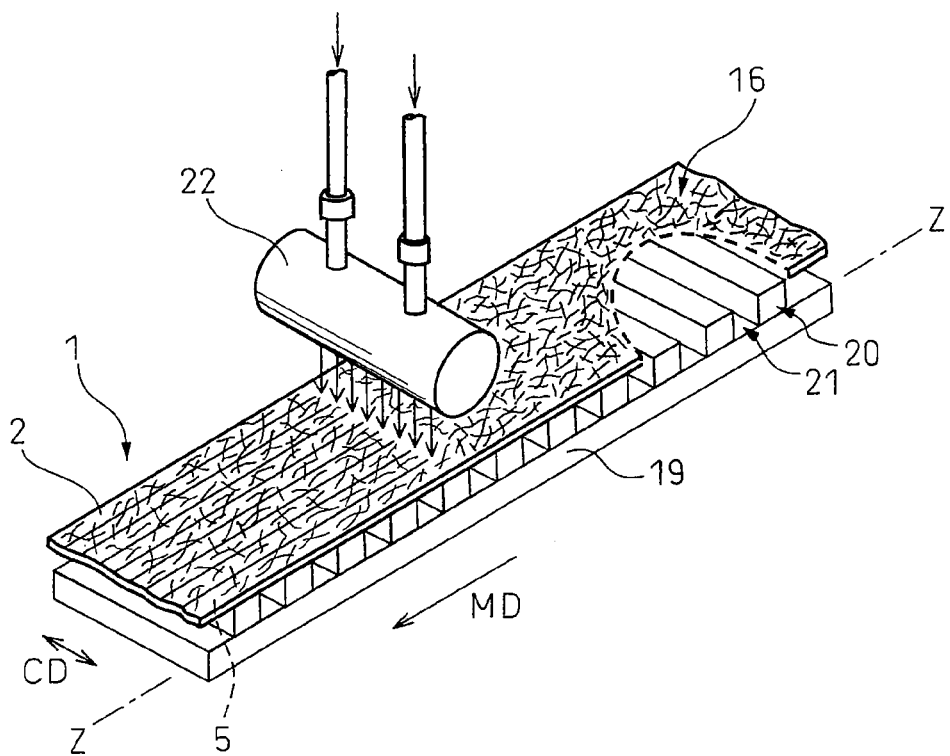
FIG. 10 is a diagram showing an example of a support for a nonwoven fabric, used on a conveyor.

FIG. 10 is a diagram showing an example of a support used on a conveyor.

The support 19 shown in FIG. 10 has protrusions 20 and depressions 21 running parallel in the cross-machine direction CD, and the protrusions 20 and depressions 21 are arranged in an alternating fashion in the machine direction MD. A fluid nozzle 22 is also shown in FIG. 10, and below the fluid nozzle 22 under the support 19 there is provided a suction section (not shown) that receives fluid. In the support 19 shown in FIG. 10, the protrusions 20 and depressions 21 have cubic shapes, and are disposed in an alternating fashion.

Also, the protrusions 20 and depressions 21 in FIG. 10 are arranged parallel to the cross-machine direction CD and alternating in the machine direction MD. However, there are no particular restrictions on the shapes and arrangement of the protrusions and depressions in the method in accordance with another embodiment of the disclosure, and for example, the protrusions and depressions: (i) may be protrusions and depressions that are all parallel to the machine direction and alternatingly disposed in the cross-machine direction, (ii) may be protrusions and depressions that are slanted with respect to the machine direction and alternatingly disposed in the direction perpendicular to the slanted direction, or (iii) may be protrusions and/or depressions having predetermined shapes (for example, cubic, cylindrical or hemispherical) that are disposed in a predetermined arrangement (for example, a heart-shaped or star-shaped arrangement).

When a support having protrusions and depressions is used, it is possible to form a nonwoven fabric with a larger plurality of protrusions and deeper plurality of recesses (with one or more open holes depending on the case), than when using a support without protrusions and depressions.

This phenomenon will be concretely described with reference to FIG. 10. When the fluid sprayed from the fluid nozzle 22 impacts the protrusions 20, it flows into and around the depressions 21. As a result, stretched extendable fiber with a high degree of freedom moves toward the depressions 21 with the flow of the fluid, and therefore primarily only elastic fiber remains at the locations where the fluid and protrusions 20 cross, so that compactness of the fibers is reduced and a plurality of recesses are formed on the second side 5. Although the elastic fiber temporarily stretches by the force of the fluid, when stress stops at less than the elastic limit, it is restored to its original form as a rule after the fluid is gone and stress is no longer applied. Therefore, the plurality of recesses on the second side 5 are rich in elastic fiber. When the fluid-blasting force is strong, the elastic fiber will also move to a certain degree, and one or more open holes are formed connecting the recesses of the first side 2 and the recesses of the second side 5.

Since the stretched extendable fiber aggregates at locations where the fluid and the depressions 21 cross, the fiber is compacted and forms a plurality of protrusions on the second side 5, and the plurality of protrusions on the second side 5 are rich in extendable fiber. In the case of FIG. 10, the second direction is the direction of the protrusions 20 and depressions 21, i.e. the cross-machine direction CD. Since the stretched extendable fibers tend to rise in the thickness direction of the nonwoven fabric at the plurality of protrusions on the second side 5, the nonwoven fabric is imparted with compression resistance and also an improved fluid take-up property. In addition, since the nonwoven fabric comprising extendable fiber and elastic fiber 1 shown in FIG. 10 has a plurality of protrusions on the second side 5, it has excellent air permeability, and especially air permeability in the planar direction, and superior feel on the skin due to reduced contact area.

A nonwoven fabric formed using a support having protrusions and depressions has on the second side a plurality of protrusions that are higher and a plurality of recesses that are deeper, compared to one formed without using such a support, and it therefore exhibits excellent air permeability, and especially air permeability in the planar direction, as well as excellent compression resistance, fluid take-up properties and feel on the skin. The plurality of protrusions on the second side are composed mainly of extendable fiber having relatively high fiber strength, and they therefore have high strength and resistance to crushing. When the nonwoven fabric formed using a support having protrusions and depressions has one or a plurality of open holes, the air permeability in the thickness direction is excellent.

Of the air permeability in the planar directions, the nonwoven fabric formed using the support shown in FIG. 10 has particularly excellent air permeability in the cross-machine direction. This is because the locations of the nonwoven fabric corresponding to the protrusions of the support (the recesses on the second side of the nonwoven fabric) can serve as gas channels.

The protrusions preferably have lower fluid permeability than the fluid permeability of the depressions. This is because with low fluid permeability at the protrusions, the fluid impacting the protrusions will flow toward the depressions, thus allowing formation of a plurality of protrusions of greater height on the second side of the nonwoven fabric comprising extendable fiber and elastic fiber, which has been formed by the method in accordance with an embodiment of the disclosure.

The material of the protrusions may be metal, plastic or the like.

There are no particular restrictions on the protrusions and depressions, and for example, they may be formed by placing a cubic or tubular metal over a metal or plastic conveyor net, paper making web, punching plate or the like that is commonly used as a fluid-permeable support, in a predetermined arrangement, such as holding them at a prescribed spacing.

Examples of supports having protrusions and/or depressions with predetermined shapes (for example, cubic, cylindrical or hemispherical) disposed in a predetermined arrangement (for example, a heart-shaped or star-shaped arrangement) include supports having hemispherical metal situated in a predetermined arrangement (such as a heart-shaped arrangement) on a punching plate. When such a support is used, it is possible to form a nonwoven fabric having recesses in a predetermined pattern (for example, heart-shaped) on the second side.

Also, by using a support with protrusions and depressions, in which hemispherical dent shapes are disposed in a predetermined arrangement (such as a heart shape) on a punching plate, it is possible to form a nonwoven fabric having a plurality of protrusions in a predetermined pattern (such as a heart shape) on the second side.

When the fluid treatment step is to be carried out on a roll, a roll-like support may be used, having the outer periphery constructed of a fluid-permeable material, such as a mesh and having protrusions and depressions situated with predetermined shapes and a predetermined arrangement, on the peripheral surface. The predetermined shapes and arrangement may be the shapes and arrangement described above.

Figure 11:
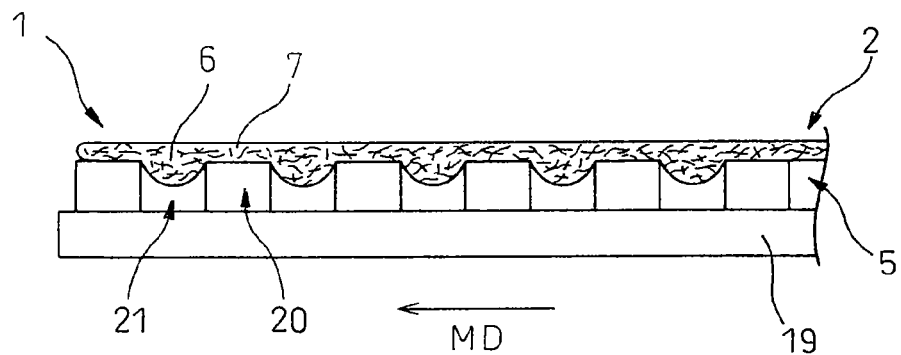
FIG. 11 is a diagram illustrating an example of a nonwoven fabric with irregularities, formed using the support shown in FIG. 8.

FIG. 11 is a diagram showing a nonwoven fabric comprising extendable fiber and elastic fiber 1 formed using the support 19 shown in FIG. 10. FIG. 11 corresponds to a cross-section along Z-Z in FIG. 10. In FIG. 11, the protrusions 6 of the second side 5 are formed in the depressions 21 of the support 19, while the recesses 7 of the second side 5 are formed on the protrusions 20 of the support 19.

Figure 12:
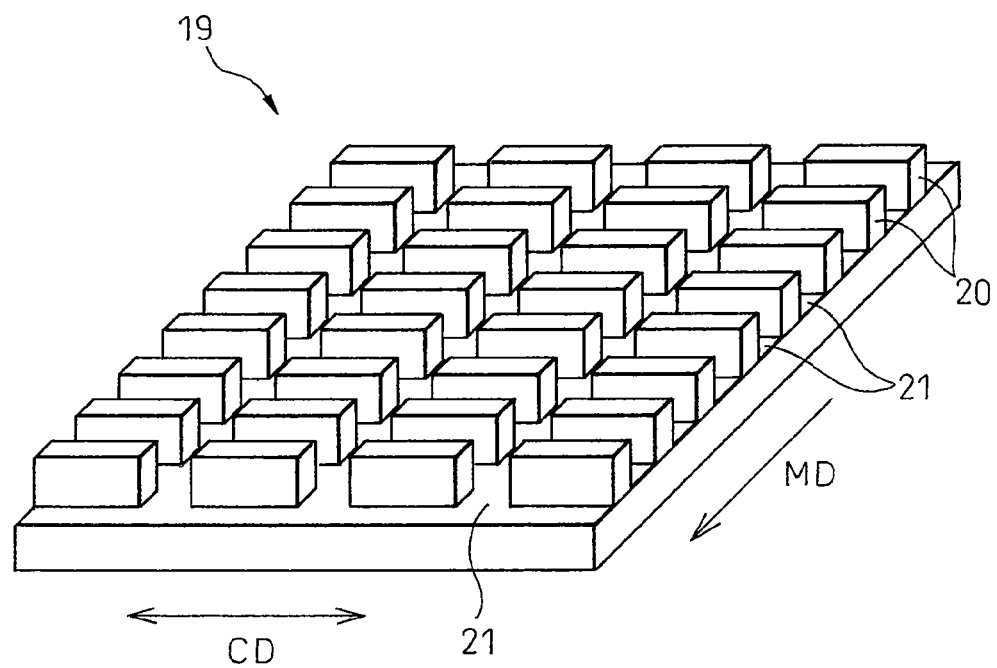
FIG. 12 is a diagram showing another example of a support for a nonwoven fabric, used on a conveyor.

In the method in accordance with another embodiment of the disclosure, the support 19 shown in FIG. 12 may be used. The protrusions 20 and depressions 21 have cubic and lattice shapes, respectively, in the support 19 shown in FIG. 12, and the protrusions 20 are disposed in an arrangement with a fixed spacing in the machine direction and the cross-machine direction.

When a support such as shown in FIG. 12 is used, a plurality of protrusions 6 and one recess 7 are formed on the second side.

In a support having protrusions and depressions, their widths will differ depending on the properties required for the nonwoven fabric that is to be formed, but as an example, the support shown in FIG. 10 preferably has protrusion widths in the range of about 0.5 to about 10 mm, and depression widths in the range of about 1 to about 10 mm.

The nonwoven fabric comprising extendable fiber and elastic fiber has an air permeability in the thickness direction of preferably at least about 400 $m^3/m^2/min$, more preferably at least about 600 $m^3/m^2/min$ and even more preferably at least about 1000 $m^3/m^2/min$. A higher air permeability in the thickness direction will prevent mustiness when the fabric is used at sites in contact with the human body.

The nonwoven fabric comprising extendable fiber and elastic fiber also has an air permeability in the planar direction of preferably at least about 5 $m^3/m^2/min$, more preferably at least about 10 $m^3/m^2/min$ and even more preferably at least about 15 $m^3/m^2/min$. A higher air permeability in the horizontal direction will prevent high-humidity air from accumulating near the skin and help it to be removed to the outside.

The nonwoven fabric comprising extendable fiber and elastic fiber of the disclosure is useful as an absorbent article, such as a sanitary product or disposable diaper, a cleaning product, such as a wiper, or a medical good, such as a mask.

Also, elastic nonwoven fabrics are sometimes used as outer sheets for disposable diapers, but since the nonwoven fabric comprising extendable fiber and elastic fiber of the disclosure which contains elastic fiber exhibits elasticity, it can be used as an outer sheet instead of the aforementioned elastic nonwoven fabrics. When the nonwoven fabric comprising extendable fiber and elastic fiber of the disclosure is used as the outer sheet for a disposable diaper, the high water absorbing property and quick-drying property of the outer sheet allows sweat produced by the user to be rapidly absorbed through the outer sheet, so that it can be transpired out of the disposable diaper, resulting in satisfactory maintenance of the environment inside the disposable diaper.

EXAMPLES

The disclosure will now be explained in greater detail using examples and comparative examples, with the understanding that the disclosure is in no way limited by the examples.

The evaluated properties and measuring conditions in the examples and comparative examples were as follows.

[Basis Weight]

The basis weight was measured in accordance with JIS L 1906, 5.2.

[Bulk]

The bulk was measured using a THICKNESS GAUGE UF-60 by Daiei Kagaku Seiki Mfg. Co., Ltd.

[Air Permeability]

The air permeability was measured using a KES-F8-AP1 air permeability tester by Kato Tech Corp., with calculation in units of $m^3/m^2/min$.

The air permeability in the thickness direction of the nonwoven fabric was measured by setting the nonwoven fabric, cut to a size of 100 mm×100 mm, in the air permeability tester.

The air permeability in the planar direction of the nonwoven fabric was measured with the nonwoven fabric cut to a size of 100 mm×100 mm and set in the air permeability tester, a 100 mm×100 mm acrylic board set thereover and application of a pressure of 3.5 $mN/cm^2$.

[Expansion Property]

This was measured using a Model AG-1KNI autograph tensile tester by Shimadzu Corp., with the following cycle.

—50% Stretch Strength—

A sample with a width of 50 mm was anchored with chucks at a chuck distance of 100 mm, and marks made at the ends of 2 chucks. The sample was then stretched to an elongation of 100% at a rate of 100 mm/min (out) and then restored to the original length at a rate of 100 mm/min (in) (1 cycle). The strength per 50 mm width during 50% outward stretching was recorded as the 50% stretch strength.

—Recovery Factor after 1 Cycle—

The aforementioned cycle was carried out once, and then the length between the marks L (mm) was measured and the recovery factor after 1 cycle was calculated by the following formula.

Recovery factor after 1 cycle (%)=100×[100−(L−100)]/100

The 50% stretch strength is preferably no greater than about 10N. If the strength exceeds about 10N, for use in a disposable diaper, for example, the diaper will be resistant to stretching during wear and will be difficult to put on. Throughout the present specification, the strength (N) per 50 mm width will be abbreviated as N/50 mm.

The recovery factor after 1 cycle is preferably at least about 50%. This is because a small value for the recovery factor after 1 cycle, with use in a disposable diaper or the like, may result in loss of elasticity of the nonwoven fabric and falling of the disposable diaper.

[Proportion of Extendable Fiber]

The nonwoven fabric was cut to a size of 50 mm×50 mm, and fiber near the top part of a protrusion on the second side (hereunder referred to as "protrusion fiber") was cut out with a cutter. The fiber in the protrusion was then weighed, immersed in 20 mL of dimethylacetamide, and allowed to stand at room temperature for 30 minutes. The remaining fiber was then filtered out, rinsed with ethanol and dried. The proportion of extendable fiber was calculated from the dry mass of the remaining fiber.

The proportion of extendable fiber was calculated in the same manner for fiber near the bottom section of the recesses on the second side as well.

Production Example 1

Production of Nonwoven Fabric

A spunbond nonwoven fabric, comprising polypropylene fiber as the extendable fiber and polyurethane elastomer fiber as the elastic fiber, was purchased. The polypropylene fiber had a fiber diameter of about 21 μm, the polyurethane elastomer fiber had a fiber diameter of about 25 μm, and the mass ratio of the polypropylene fiber and polyurethane fiber was about 50:50. During spinning, the polypropylene fiber was hydrophilized by mixture of a nonionic hydrophilic agent at 0.3 mass % with respect to the mass of the polypropylene fiber, but the polyurethane elastomer fiber was not hydrophilized.

The properties of the spunbond nonwoven fabric are shown in Table 1.

—Gear Stretching Treatment—

The spunbond nonwoven fabric was reeled out at a speed of 30 m/min and subjected to gear stretching using a gear stretcher such as shown in FIG. 7 (gear pitch: 4.9 mm, gear tooth cutting depth: 7.0 mm, gear tip width: 0.2 mm, gear temperature: 55° C.), to a stretch ratio of 203% in the machine direction MD, to form a nonwoven fabric having high-stretch regions and low-stretch regions.

In the nonwoven fabric having high-stretch regions and low-stretch regions, embossed sections remained in the low-stretch regions that were in contact with the tips of the teeth. In the high-stretch regions that were not in contact with the tips of the teeth, some of the embossed sections had been crushed, forming web regions.

The properties of the nonwoven fabric having high-stretch regions and low-stretch regions are shown in Table 1.

—Hydrophilic Agent Treatment—

The nonwoven fabric having high-stretch regions and low-stretch regions was placed on a support comprising a round-hole, 60° zigzag-type punching plate (φ:3.0 mm, MD pitch: 6.93 mm, CD pitch: 4.0 mm, thickness: 1.0 mm), and the nonwoven fabric having high-stretch regions and low-stretch regions was spray coated with a 2.5 mass % aqueous solution of a sucrose fatty acid ester as a hydrophilic agent-containing solution, to a sucrose fatty acid ester basis weight of about 0.1 g/m².

—Steam Treatment—

Next, the nonwoven fabric having high-stretch regions and low-stretch regions, which had been coated with the hydrophilic agent, was passed through a steam treatment system comprising a plurality of nozzles (φ: 0.5 mm) at 1.0 mm spacings (spray pressure: 0.25 Mpa, water vapor temperature: approximately 125° C.), at a speed of 30 m/min while maintaining a distance of 4.0 mm between the nozzles and support, to obtain a nonwoven fabric 1.

The properties of the nonwoven fabric 1 are shown in Table 1.

Production Examples 2 and 3

Nonwoven fabrics 2 and 3 were obtained in the same manner as Production Example 1, except that the basis weights of the initial spunbond nonwoven fabrics were different. The properties of the nonwoven fabrics 2 and 3 are shown in Table 1.

Reference Production Example 1

A nonwoven fabric 4 was obtained in the same manner as Production Example 1, except that no hydrophilic agent treatment was carried out. The properties of the nonwoven fabric 4 are shown in Table 1.

Comparative Production Example 1

A nonwoven fabric 5 was obtained in the same manner as Production Example 1, except that in the initial spunbond fabric, the polypropylene fiber contained no hydrophilic agent and the basis weight was different, and also no hydrophilic agent treatment was carried out. The properties of the nonwoven fabric 5 are shown in Table 1.

Comparative Production Example 2

A nonwoven fabric 6 was formed by the method described in PTL 1. The properties of the nonwoven fabric 6 are shown in Table 1.

Examples 1-3, Reference Example 1 and Comparative Examples 1 and 2

Nonwoven fabrics 1 to 6 were subjected to a water absorption test and the water absorption height was measured. The water absorption test was conducted in the manner described above. The results are shown in Table 1.

Nonwoven fabrics 1 to 6 were each then subjected to a transpiration test and the transpiration rate was measured. The transpiration test was conducted in the manner described above. For the transpiration test, the nonwoven fabric was placed on the watch glass with the support side of the nonwoven fabric contacting the physiological saline. The results are shown in Table 1.

TABLE 1

| | | Example No. | | | | | |
|---|---|---|---|---|---|---|---|
| | | Example 1 | Example 2 | Example 3 | Ref. Example 1 | Comp. Example 1 | Comp. Example 2 |
| Nonwoven fabric No. | | Nonwoven fabric 1 | Nonwoven fabric 2 Initial | Nonwoven fabric 3 | Nonwoven fabric 4 | Nonwoven fabric 5 | Nonwoven fabric 6 |
| Fiber with hydrophilic agent | | Extendable fiber | Extendable fiber | Extendable fiber | Extendable fiber | — | — |
| Basis weight | g/m² | 51.9 | 40.1 | 30.4 | 51.9 | 29.6 | |
| Bulk | mm | 0.36 | 0.31 | 0.26 | 0.36 | 0.22 | |
| Permeability (thickness direction) | m³/m²/min | 190 | 188 | 464 | 190 | — | |
| Permeability (planar direction) | m³/m²/min | 1 | 1 | 1 | 1 | — | |
| Water absorption height | mm | 4 | 4 | 0 | 4 | 0 | |
| Transpiration rate | % | 58.0 | 63.5 | 59.1 | 58.0 | — | |
| 50% stretch strength (MD) | 5/50 mm | 16.8 | 12.6 | 10.2 | 16.8 | 20.4 | |
| Gear stretching treatment | | | | | | | |
| Gear stretching treatment | | Yes | Yes | Yes | Yes | Yes | No |
| Basis weight | g/m² | 53.6 | 41.7 | 30.7 | 53.6 | 33.7 | |
| Bulk | mm | 1.01 | 0.86 | 0.70 | 1.01 | 0.92 | |
| Permeability (thickness direction) | m³/m²/min | 410 | 500 | 870 | 410 | 644 | |
| Permeability (planar direction) | m³/m²/min | 13 | 11 | 9 | 13 | 8 | |
| Water absorption height | mm | 2 | 2 | 0 | 2 | 0 | |
| Transpiration rate | % | 17.5 | 25.4 | 19.3 | 17.5 | 16.7 | |

TABLE 1-continued

| | | Example 1 | Example 2 | Example 3 | Ref. Example 1 | Comp. Example 1 | Comp. Example 2 |
|---|---|---|---|---|---|---|---|
| 50% stretch strength (MD) | N/50 mm | 2.1 | 1.5 | 1.1 | 2.1 | 1.3 | |
| Recovery after 1 cycle | 1 | 91.6 | 92.3 | 92.2 | 91.6 | 91.4 | |
| Hydrophilic agent treatment | | | | | | | |
| Hydrophilic agent treatment | | Yes | Yes | Yes | No | No | No |
| Steam treatment | | | | | | | |
| Steam treatment | | Yes | Yes | Yes | Yes | No | No |
| Basis weight | g/m² | 54.3 | 42.1 | 31.5 | 52.1 | 33.7 | 71.9 |
| Bulk | mm | 0.94 | 0.85 | 0.72 | 0.94 | 0.92 | 1.64 |
| Permeability (thickness direction) | m³/m²/min | 400 | 750 | 1330 | 370 | 640 | 190 |
| Permeability (planar direction) | m³/m²/min | 21 | 18 | 17 | 26 | 8 | 23 |
| Water absorption height | mm | 35 | 20 | 11 | 0 | 0 | 11 |
| Transpiration rate | % | 62.5 | 46.0 | 25.5 | 18.8 | 16.7 | 92.6 |
| 50% stretch strength (MD) | N/50 mm | 2.6 | 1.8 | 1.6 | 1.9 | 1.3 | 12.8 |
| Recovery after 1 cycle | % | 93.3 | 92.0 | 93.3 | 89.2 | 91.4 | Breakage |

Nonwoven fabrics 1 to 3 of Examples 1 to 3 had excellent air permeability in the planar direction and thickness direction, and also had high water absorbing and quick-drying properties.

The nonwoven fabrics 1 to 3 that had been coated with a hydrophilic agent had higher water absorbing and quick-drying properties compared to the nonwoven fabric of Reference Example 1, i.e. a nonwoven fabric which had the hydrophilic agent only on the extendable fiber.

Example 4

Measurement of Proportion of Extendable Fiber

—Production of Nonwoven Fabric—

A spunbond nonwoven fabric comprising polyolefin fiber (fiber diameter: approximately 21 μm) as the extendable fiber and polyurethane fiber (fiber diameter: 25 μm) as the elastic fiber in a proportion of about 50:50 was purchased.

—Gear Stretching Treatment—

The spunbond nonwoven fabric was reeled out at a speed of 10 m/min and passed through 4 preheated rolls that had been preheated to 80° C., and then subjected to gear stretching with the gear stretcher shown in FIG. 8 (gear pitch: 2.5 mm, gear tooth cutting depth: 3.0 mm, stretch ratio: 160%), after which it was subjected to gear stretching with the gear stretcher shown in FIG. 7 (gear pitch: 4.9 mm, gear tooth cutting depth: 7.0 mm, stretch ratio: 202%), to form a nonwoven fabric having high-stretch regions and low-stretch regions. The gear temperature of both gear stretchers was 55° C.

In the nonwoven fabric having high-stretch regions and low-stretch regions, embossed sections remained in the low-stretch regions that were in contact with the tips of the teeth. In the high-stretch regions that were not in contact with the tips of the teeth, some of the embossed sections had been crushed, forming web regions.

—Steam Treatment—

The nonwoven fabric having high-stretch regions and low-stretch regions was placed on a support having protrusions and depressions each parallel to the cross-machine direction, and alternating in the machine direction, such as shown in FIG. 10. The protrusions did not transmit the fluid, and their widths and heights were 3 mm and 5 mm, respectively. The widths of the depressions were 2 mm. The gear treated nonwoven fabric was then passed through a steam treatment system comprising a plurality of nozzles (φ: 0.5 mm) at a spacing of 2.0 mm, at a speed of 5 m/min, to obtain nonwoven fabrics 7 to 9. The nonwoven fabrics 7 to 9 had a plurality of open holes.

For evaluation of the proportion of extendable fiber, the hydrophilic agent-coating step was omitted. This is because it is believed that the proportion of extendable fiber does not change with or without the hydrophilic agent-coating step, and that coating of the nonwoven fabric with the hydrophilic agent can produce error in measurement of the proportion of extendable fiber.

The conditions of pressure and water vapor temperature in the steam treatment system are shown in Table 2 below, together with the properties of the nonwoven fabrics 7 to 9.

TABLE 2

| | Steam treatment | | Basis weight (g/m²) | Bulk (mm) | Permeability (m³/m²/min) | |
|---|---|---|---|---|---|---|
| Nonwoven fabric | Pressure (MPa) | Temp. (° C.) | | | Thickness direction | Planar direction |
| Nonwoven fabric 7 | 0.3 | 131 | 37.1 | 0.86 | 1350 | 14 |
| Nonwoven fabric 8 | 0.5 | 149 | 38.7 | 0.95 | 1140 | 26 |
| Nonwoven fabric 9 | 0.7 | 162 | 37.2 | 0.89 | 2060 | 31 |

The proportion of polyolefin fiber as extendable fiber in the nonwoven fabrics 7 to 9 was evaluated by a dyeing method.

Nonwoven fabrics 7 to 9 were dyed with a dye that colors polyurethane fiber red and does not color polyolefin fiber, and were visually evaluated with an optical microscope. As a result, all of the nonwoven fabrics 7 to 9 were confirmed to have polyolefin fiber as extendable fiber and polyurethane fiber as elastic fiber respectively maldistributed on the first side and second side, as shown in FIGS. 3 and 4. More specifically, it was confirmed that the proportion of polyolefin fiber in the protrusions on the first side was higher than the proportion of polyurethane fiber in the recesses on the first side, and the proportion of the polyolefin fiber in the protrusions on the second side was higher than the proportion of polyurethane fiber in the recesses on the second side.

The proportion of polyolefin fiber in the protrusions on the second side and the recesses on the second side of the nonwoven fabric 9 was also evaluated by a solvent method. When the protrusions in the second side and the recesses on the second side were sampled in amounts of 67.7 mg and 39.8 mg, respectively, and evaluated using 20 mL of dimethylacetamide as the solvent, the proportion of polyolefin fiber in the protrusions on the second side and the recesses on the second side were 54 mass % and 43 mass %, respectively. These results confirmed that the proportion of polyolefin fiber in the protrusions on the second side of the nonwoven fabric 9 was higher than the proportion of polyolefin fiber in the recesses on the second side.

The proportion of polyolefin fiber in the spunbond nonwoven fabric was 50 mass %.

Figure 13:
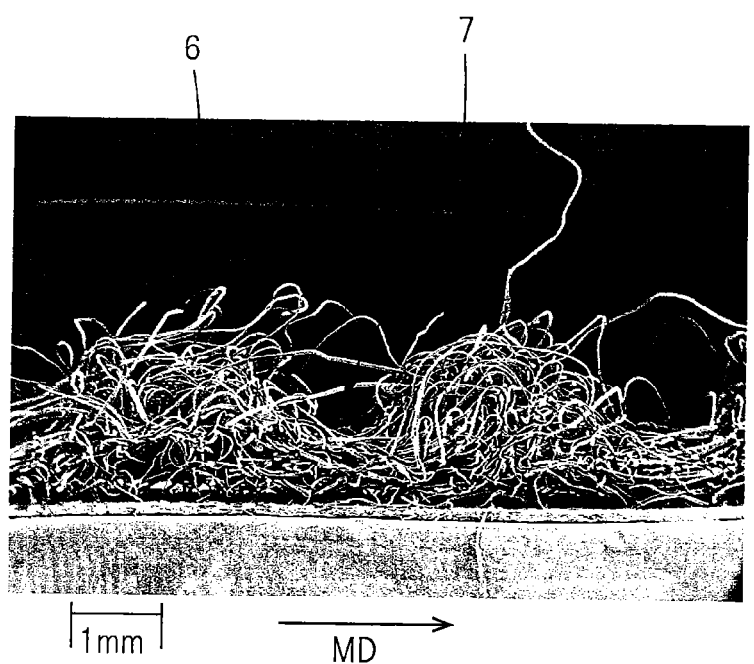
FIG. 13 is a photomicrograph showing a cross-section of the nonwoven fabric 2 formed in Example 1 in the MD direction.

FIG. 13 shows an electron micrograph of a cross-section of the nonwoven fabric 7 in the MD direction.

Protrusions 6 and recesses 7 are shown in FIG. 13 which is a cross-section in the machine direction MD, and it is seen that the fiber content per unit area is high and the fibers are standing in the protrusions 6, while the fiber content per unit area is low and the fibers are compressed in the recesses 7.

Specifically, the present disclosure relates to the following aspects.

[Aspect 1]

A nonwoven fabric comprising extendable fiber and elastic fiber, wherein the nonwoven fabric comprises a first side having a plurality of protrusions and a plurality of recesses and a second side on the side opposite the first side, the proportion of extendable fiber in the protrusions on the first side is higher than the proportion of extendable fiber in the recesses on the first side, and the nonwoven fabric is coated with a hydrophilic agent, or the extendable fiber and elastic fiber comprise a hydrophilic agent, the nonwoven fabric has a water absorbing property represented by a water absorption height of at least 10 mm in a water absorption test, and a quick-drying property represented by a transpiration rate of at least 20 mass % in a transpiration test.

[Aspect 2]

The nonwoven fabric according to aspect 1, wherein the second side has a plurality of protrusions and recesses, and the proportion of extendable fiber in the protrusions on the second side is higher than the proportion of extendable fiber in the recesses on the second side.

[Aspect 3]

The nonwoven fabric according to aspect 2, which has one or a plurality of open holes connecting the recesses on the first side and the recesses on the second side.

[Aspect 4]

The nonwoven fabric according to any one of aspects 1 to 3, wherein the nonwoven fabric is coated with a hydrophilic agent, and the extendable fiber comprises a hydrophilic agent.

[Aspect 5]

A nonwoven fabric according to any one of aspects 1 to 4, wherein the water absorption height in a water absorption test is at least 18 mm.

[Aspect 6]

The nonwoven fabric according to any one of aspects 1 to 5, wherein the transpiration rate in a transpiration test is at least 40 mass %.

[Aspect 7]

The nonwoven fabric according to any one of aspects 1 to 6, wherein the air permeability in the thickness direction is 400 $m^3/m^2$/min or greater, and the air permeability in the planar direction is 5 $m^3/m^2$/min or greater.

[Aspect 8]

The nonwoven fabric according to any one of aspects 1 to 7, wherein the material of the extendable fiber is selected from the group consisting of polyolefins, polystyrenes, polyesters, polyamides, polyurethanes, polylactic acid, and combinations thereof.

[Aspect 9]

The nonwoven fabric according to any one of aspects 1 to 8, wherein the material of the elastic fiber is selected from the group consisting of polyurethane-based elastomers, polystyrene-based elastomers, polyolefin-based elastomers, polyamide-based elastomers, polyester-based elastomers, and combinations thereof.

[Aspect 10]

The nonwoven fabric according to any one of aspects 1 to 9, wherein the hydrophilic agent is selected from the group consisting of anionic hydrophilic agents, cationic hydrophilic agents, nonionic hydrophilic agents, and combinations thereof.

[Aspect 11]

A method for producing a nonwoven fabric comprising extendable fiber and elastic fiber, comprising the steps of:

providing a nonwoven fabric to be treated which comprises extendable fiber and elastic fiber, non-homogeneous stretching of the nonwoven fabric to be treated which comprises extendable fiber and elastic fiber, to form a nonwoven fabric with high-stretch regions and low-stretch regions, coating a hydrophilic agent-containing solution onto the nonwoven fabric with the high-stretch regions and low-stretch regions, and placing the nonwoven fabric with high-stretch regions and low-stretch regions on which the hydrophilic agent has been coated on a support and spraying a fluid thereon, to form a nonwoven fabric comprising extendable fiber and elastic fiber.

[Aspect 12]

The method according to aspect 11, wherein the step of non-homogeneous stretching is carried out by passing the nonwoven fabric comprising the extendable fiber and elastic fiber through the gap between a pair of gear rolls with rotational axis lines that are perpendicular to the direction of transport, and rotating while a plurality of teeth situated on the peripheral surfaces of each of the gear rolls are mutually engaged.

[Aspect 13]

The method according to aspect 11 or 12, wherein the hydrophilic agent solution is an aqueous hydrophilic agent solution.

[Aspect 14]

The method according to any one of aspects 11 to 13, wherein the fluid is selected from the group consisting of air, water vapor and water.

REFERENCES SIGNS LIST

1 Nonwoven fabric comprising extendable fiber and elastic fiber
2 First side
3 Protrusion
4 Recess
5 Second side
6 Protrusion
7 Recess
8 Open hole
9 Hydrophilic agent
11 Gear stretcher
12, 12' Gear rolls
13, 13' Peripheral surfaces
14, 14' Teeth
15 Nonwoven fabric to be treated which comprises extendable fiber and elastic fiber
16 Nonwoven fabric having high-stretch regions and low-stretch regions
17 Gear pitch
18 Gear tooth cutting depth
19 Support
20 Protrusion
21 Depression
22 Fluid nozzle
EX Extendable fiber
EL Elastic fiber
A First direction
B Second direction
MD Machine direction
CD Cross-machine direction

The invention claimed is:

1. A nonwoven fabric comprising extendable fiber and elastic fiber,
wherein the nonwoven fabric comprises a first side having a plurality of protrusions and a plurality of recesses and a second side on the side opposite the first side, the proportion of extendable fiber in the protrusions on the first side is higher than the proportion of extendable fiber in the recesses on the first side,
wherein the nonwoven fabric has high-stretch regions and low-stretch regions, in which the high-stretch regions have a degree of stretch of the stretched extendable fiber which is higher than in the low-stretch regions, and the low-stretch regions have a degree of stretch of the stretched extendable fiber which is lower than in the high-stretch regions,
the nonwoven fabric is coated with a hydrophilic agent, or the extendable fiber and elastic fiber comprise a hydrophilic agent, the nonwoven fabric has a water absorbing property represented by a water absorption height of at least 10 mm in a water absorption test, and a quick-drying property represented by a transpiration rate of at least 20 mass % in a transpiration test, and
wherein the second side has a plurality of protrusions and recesses, and the proportion of extendable fiber in the protrusions on the second side is higher than the proportion of extendable fiber in the recesses on the second side.

2. The nonwoven fabric according to claim 1, which has one or a plurality of open holes connecting the recesses on the first side and the recesses on the second side.

3. The nonwoven fabric according to claim 1, wherein the nonwoven fabric is coated with a hydrophilic agent, and the extendable fiber comprises a hydrophilic agent.

4. The nonwoven fabric according to claim 1, wherein the water absorption height in a water absorption test is at least 18 mm.

5. The nonwoven fabric according to claim 1, wherein the transpiration rate in a transpiration test is at least 40 mass %.

6. The nonwoven fabric according to claim 1, wherein the air permeability in the thickness direction is 400 m3/m2/min or greater, and the air permeability in the planar direction is 5 m3/m2/min or greater.

7. The nonwoven fabric according to claim 1, wherein the material of the extendable fiber is selected from the group consisting of polyolefins, polystyrenes, polyesters, polyamides, polyurethanes, polylactic acid, and combinations thereof.

8. The nonwoven fabric according to claim 1, wherein the material of the elastic fiber is selected from the group consisting of polyurethane-based elastomers, polystyrene-based elastomers, polyolefin-based elastomers, polyamide-based elastomers, polyester-based elastomers, and combinations thereof.

9. The nonwoven fabric according to claim 1, wherein the hydrophilic agent is selected from the group consisting of anionic hydrophilic agents, cationic hydrophilic agents, nonionic hydrophilic agents, and combinations thereof.

10. A method for producing a nonwoven fabric comprising extendable fiber and elastic fiber, comprising the steps of:
providing a nonwoven fabric to be treated which comprises extendable fiber and elastic fiber,
non-homogeneous stretching of the nonwoven fabric to be treated which comprises extendable fiber and elastic fiber, to form a nonwoven fabric with high-stretch regions and low-stretch regions, wherein the high-stretch regions have a degree of stretch of the stretched extendable fiber which is higher than in the low-stretch regions, and the low-stretch regions have a degree of stretch of the stretched extendable fiber which is lower than in the high-stretch regions,
coating a hydrophilic agent-containing solution onto the nonwoven fabric with the high-stretch regions and low-stretch regions, and
placing the nonwoven fabric with high-stretch regions and low-stretch regions on which the hydrophilic agent has been coated on a support having protrusions and depressions and spaying a fluid thereon, to form the nonwoven fabric comprising extendable fiber and elastic fiber.

11. The method according to claim 10, wherein the step of non-homogeneous stretching is carried out by passing the nonwoven fabric comprising the extendable fiber and elastic fiber through the gap between a pair of gear rolls with rotational axis lines that are perpendicular to the direction of transport, and rotating while a plurality of teeth situated on the peripheral surfaces of each of the gear rolls are mutually engaged.

12. The method according to claim 10, wherein the hydrophilic agent solution is an aqueous hydrophilic agent solution.

13. The method according to claim 10, wherein the fluid is selected from the group consisting of air, water vapor and water.

14. The nonwoven fabric according to claim 1, wherein the nonwoven fabric is coated with a hydrophilic agent, and the extendable fiber comprises a hydrophilic agent.

15. The nonwoven fabric according to claim 2, wherein the nonwoven fabric is coated with a hydrophilic agent, and the extendable fiber comprises a hydrophilic agent.

16. The nonwoven fabric according to claim 1, wherein the water absorption height in a water absorption test is at least 18 mm.

17. The nonwoven fabric according to claim 2, wherein the water absorption height in a water absorption test is at least 18 mm.

18. The nonwoven fabric according to claim 3, wherein the water absorption height in a water absorption test is at least 18 mm.

19. The nonwoven fabric according to claim 12, wherein the water absorption height in a water absorption test is at least 18 mm.

\* \* \* \* \*

UNITED STATES PATENT AND TRADEMARK OFFICE
CERTIFICATE OF CORRECTION

| | | |
|---|---|---|
| PATENT NO. | : 9,546,440 B2 | Page 1 of 1 |
| APPLICATION NO. | : 14/003073 | |
| DATED | : January 17, 2017 | |
| INVENTOR(S) | : Satoshi Mitsuno and Jun Okuda | |

It is certified that error appears in the above-identified patent and that said Letters Patent is hereby corrected as shown below:

In the Claims

In Claim 6, Column 28, Line 13, the formula should be changed from "400 m3/m2/min" and substituted with --400 $m^3/m^2$/min-- in its place.

In Claim 6, Column 28, Line 15, the formula should be changed from "m3/m2/min" and substituted with --$m^3/m^2$/min-- in its place.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*